(12) United States Patent  
Shu

(10) Patent No.: US 7,951,773 B2
(45) Date of Patent: May 31, 2011

(54) RING-CLOSING METATHESIS PROCESS FOR THE PREPARATION OF MACROCYCLIC PEPTIDES

(75) Inventor: Chutian Shu, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 580 days.

(21) Appl. No.: 12/065,927

(22) PCT Filed: Sep. 8, 2006

(86) PCT No.: PCT/US2006/034921
§ 371 (c)(1),
(2), (4) Date: Mar. 21, 2008

(87) PCT Pub. No.: WO2007/030656
PCT Pub. Date: Mar. 15, 2007

(65) Prior Publication Data
US 2008/0242835 A1 Oct. 2, 2008

Related U.S. Application Data

(60) Provisional application No. 60/715,534, filed on Sep. 9, 2005.

(51) Int. Cl.
*A62K 38/55* (2006.01)
*A61K 38/00* (2006.01)

(52) U.S. Cl. .......................... 514/4.1; 530/333; 530/335

(58) Field of Classification Search .................. None
See application file for complete search history.

(56) References Cited

U.S. PATENT DOCUMENTS

| | | | |
|---|---|---|---|
| 6,608,027 | B1 | 8/2003 | Tsantrizos et al. |
| 7,119,072 | B2 | 10/2006 | Llinas-Brunet et al. |
| 7,148,347 | B2 | 12/2006 | Brandenburg et al. |
| 2004/0248779 | A1* | 12/2004 | Dersch et al. ............... 514/9 |
| 2005/0075279 | A1 | 4/2005 | Llinas-Brunet et al. |
| 2005/0080005 | A1 | 4/2005 | Llinas-Brunet et al. |

OTHER PUBLICATIONS

Rutjes, et al; Ruthenium-Catalyzed Ring Closing Olefin Metathesis of Non-Natural alpha-Amino Acids; Tetrahedron Letters; Elsevier; Amsterdam, NL; Jan. 27, 1997; vol. 38; No. 4; pp. 677-680. Huwe, et al; A Novel Approach to Substituted Pyrrolidines and Piperidines via Olefin Metathesis; Synlett; Jan. 1996; pp. 65-66.
International Search Report, Form PCT/ISA/210, for corresponding PCT/US2006/034921.

(Continued)

*Primary Examiner* — Cecilia Tsang
*Assistant Examiner* — Thomas S Heard
(74) *Attorney, Agent, or Firm* — Michael P. Morris; Philip I. Datlow

(57) ABSTRACT

Disclosed is a process for preparing a compound of formula (I) by protecting the secondary amide nitrogen atom in the compound of formula (III) to obtain (IV) wherein $PG_N$ is a suitable nitrogen protecting group, ring-closing the compound of formula (IV) by cyclizing it in the presence of a suitable catalyst in a suitable organic solvent to obtain (V), and then deprotecting the resulting compound of formula (V) to obtain (I), as outlined in the following scheme. The compounds of formula (I) are active agents for the treatment of hepatitis C viral (HCV) infections or are intermediates useful for the preparation of anti-HCV agents.

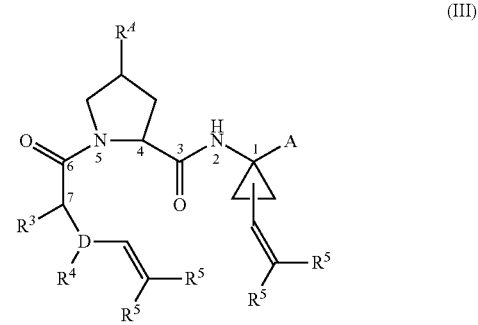

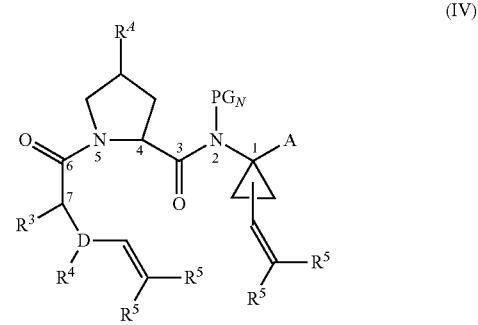

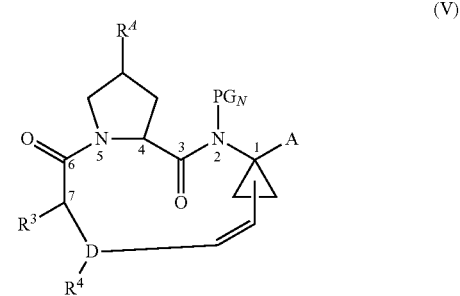

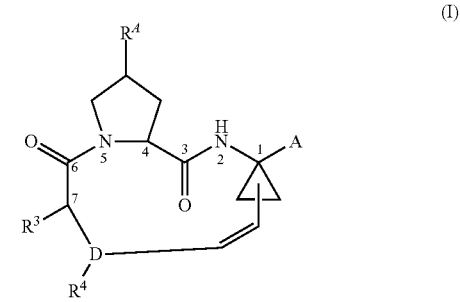

14 Claims, No Drawings

OTHER PUBLICATIONS

Goldring et al.; Synthesis of Macrocyclic Lactams and Lactones via Ring-Closing Olefin Metathesis; Tetrahedron Letters 39; 1998; pp. 4955-4958.

Creighton et al.; Synthesis of an Eight-Membered Cyclic Pseudo-Dipeptide Using Ring Closing Metathesis; Organic Letters; 2001; vol. 3; No. 6; pp. 893-895.

Vo-Thanh et al.; Ring Closing Metathesis of Unsaturated Amides as a Route to Short and Medium-Sized Unsaturated Lactams and to Ethylenic Pseudopeptides; Synlett 2001; No. 1; pp. 37-40.

* cited by examiner

RING-CLOSING METATHESIS PROCESS FOR THE PREPARATION OF MACROCYCLIC PEPTIDES

CROSS-REFERENCE TO RELATED APPLICATIONS

This application claims the benefit of U.S. Provisional Application No. 60/715,534, filed Sep. 9, 2005.

BACKGROUND OF THE INVENTION

1. Technical Field

The invention relates to an improved process for the preparation of certain macrocyclic compounds useful as agents for the treatment of hepatitis C viral (HCV) infections, or as intermediates useful in preparing such agents.

2. Background Information

The macrocyclic compounds of the following formula (I) and methods for their preparation are known from: Tsantrizos et al., U.S. Pat. No. 6,608,027 B1; Llinas Brunet et al, U.S. Application Publication No. 2003/0224977 A1; Llinas Brunet et al, U.S. Application Publication No. 2005/0075279 A1; Llinas Brunet et al, U.S. Application Publication No. 2005/0080005 A1; Brandenburg et al., U.S. Application Publication No. 2005/0049187 and Samstag et al., U.S. Application Publication No. 2004/0248779 A1:

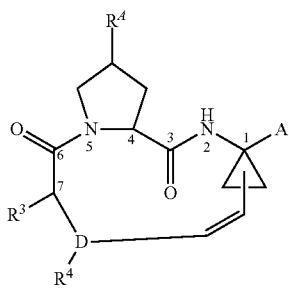

(I)

wherein
$R^4$ is OH, O-PG, where PG is a protecting group, or —OSO$_2$—$R^{27}$, wherein $R^{27}$ is selected from phenyl, p-tolyl, p-bromophenyl, p-nitrophenyl, methyl, trifluoromethyl, perfluorobutyl and 2,2,2-trifluoroethyl;
or a group of formula II

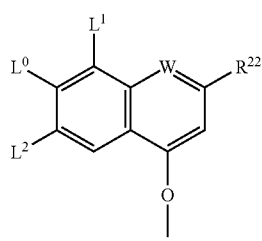

(II)

W is CH or N;
$L^0$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$,
wherein each $R^{23}$ is independently H, $C_{1-6}$ alkyl or $C_{3-6}$ cycloalkyl;

$L^1$, $L^2$ are each independently H, halogen, $C_{1-4}$alkyl, —O—$C_{1-4}$alkyl, or —S—$C_{1-4}$alkyl (the sulfur being in any oxidized state); or
$L^0$ and $L^1$ or
$L^0$ and $L^2$ may be covalently bonded to form together with the two C-atoms to which they are linked a 4-, 5- or 6-membered carbocyclic ring wherein one or two (in the case of a 5- or 6-membered ring) —CH$_2$— groups not being directly bonded to each other, may be replaced each independently by —O— or NR$^a$ wherein R$^a$ is H or $C_{1-4}$alkyl, and wherein said ring is optionally mono- or di-substituted with $C_{1-4}$ alkyl;
$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_{6 \text{ or } 10}$ aryl or Het, wherein Het is a five-, six-, or seven-membered saturated or unsaturated heterocycle containing from one to four heteroatoms selected from nitrogen, oxygen and sulfur;
said cycloalkyl, aryl or Het being substituted with $R^{24}$,
wherein $R^{24}$ is H, halo, $C_{1-6}$ alkyl, $C_{3-6}$ cycloalkyl, $C_{1-6}$ alkoxy, $C_{3-6}$ cycloalkoxy, NO$_2$, N(R$^{25}$)$_2$, NH—C(O)—R$^{25}$; or NH—C(O)—NH—R$^{25}$, wherein each $R^{25}$ is independently: H, $C_{1-6}$ alkyl or $C_{3-6}$ cycloalkyl;
or $R^{24}$ is NH—C(O)—OR$^{26}$ wherein $R^{26}$ is $C_{1-6}$ alkyl or $C_{3-6}$ cycloalkyl;
$R^3$ is hydroxy, NH$_2$, or a group of formula —N(R*)—R$^9$, wherein R* is H or a protecting group, and $R^9$ is $C_{6 \text{ or } 10}$ aryl, heteroaryl, —C(O)—R$^{20}$, —C(O)—NHR$^{20}$ or —C(O)—OR$^{20}$, wherein $R^{20}$ is $C_{1-6}$ alkyl or $C_{3-6}$ cycloalkyl;
D is a 3 to 7 atom saturated alkylene chain optionally containing one to three heteroatoms independently selected from: O, S or N—$R^{27}$, wherein $R^{27}$ is H, $C_{1-6}$alkyl, $C_{3-6}$cycloalkyl or C(O)R$^{28}$, wherein $R^{28}$ is $C_{1-6}$alkyl, $C_{3-6}$cycloalkyl or C$_6$ or 10 aryl;
$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and
A is an amide of formula —C(O)—NH—$R^{11}$, wherein $R^{11}$ is selected from the group consisting of: $C_{1-8}$ alkyl, $C_{3-6}$ cycloalkyl, $C_{6 \text{ or } 10}$ aryl, $C_{7-16}$ aralkyl, or SO$_2$R$^{5A}$ wherein R$^{5A}$ is $C_{1-8}$ alkyl, $C_{3-7}$ cycloalkyl, $C_{1-6}$ alkyl-$C_{3-7}$ cycloalkyl;
or A is a carboxylic acid or a pharmaceutically acceptable salt or ester thereof.

The compounds of formula (I) are disclosed in the above-mentioned patent documents as being active agents for the treatment of hepatitis C viral (HCV) infections, or as intermediates useful for the preparation of such anti-HCV agents as described therein, and are prepared therein via ring-closing metathesis of an acyclic diolefin using ruthenium-based catalysts in a suitable organic solvent. The disadvantages of the previously reported approaches to the compound (I) via ring-closing metathesis include long reaction time, high catalyst loading, moderate yields, and the need to use lower concentrations of the diene substrate to obtain optimum results. Thus, there is a continuing need in the art to develop improved processes for obtaining the macrocyclic compounds of formula (I).

BRIEF SUMMARY OF THE INVENTION

Surprisingly, it has been discovered that the ring-closing metathesis step can be improved by first substituting the P1 secondary amide nitrogen atom in the diene substrate with a suitable nitrogen protecting group that can be cleaved following the ring-closing step.

Accordingly, the present invention is directed to a process for preparing a compound of formula I as previously set forth, said process comprising protecting the secondary amide nitrogen atom in the compound of formula III to obtain IV wherein $PG_N$ is a suitable nitrogen protecting group, ring-closing the resulting compound of formula IV by cyclizing it in the presence of a suitable catalyst in a suitable organic solvent to obtain V, and then deprotecting the resulting compound of formula V to obtain I, as outlined in the following scheme:

to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

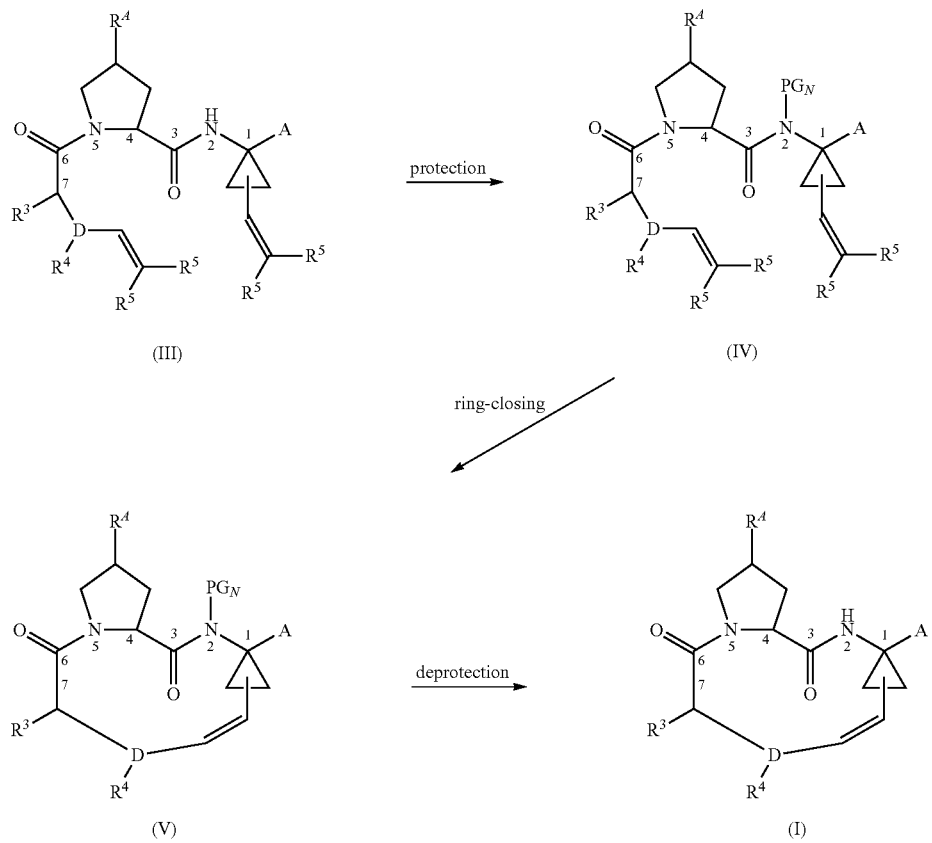

wherein the variable groups $R^A$, $R^3$, $R^4$, D and A are as defined previously and each $R^5$ is independently selected from H, $C_{1-6}$alkyl and $C_{3-6}$cycloalkyl and $PG_N$ is a nitrogen protecting group.

The improvements that may be achieved by using this modified substrate of formula IV for the ring-closing reaction include higher yield, improved efficiency, and the ability to run the reaction at higher substrate concentrations, thus increasing productivity.

DETAILED DESCRIPTION OF THE INVENTION

Definitions

Terms not specifically defined herein should be given the meanings that would be given to them by one of ordinary skill in the art in light of the disclosure and the context. As used in the present specification, however, unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or radical having 1

The term "$C_{1-x}$ alkyl" as used herein, either alone or in combination with another substituent, means acyclic, straight or branched chain alkyl substituents containing the specified 1 to x number of carbon atoms.

The term "$C_{1-x}$ alkoxy" as used herein, either alone or in combination with another substituent, means the substituent $C_{1-x}$ alkyl-O— wherein alkyl is as defined above containing up to x carbon atoms.

The term "saturated alkylene chain" as used herein means a divalent alkyl substituent derived by the removal of one hydrogen atom from each end of a saturated straight or branched chain aliphatic hydrocarbon and includes, for example, —$CH_2CH_2C(CH_3)_2CH_2CH_2$—.

The term "$C_{3-x}$ cycloalkoxy" as used herein, either alone or in combination with another substituent, means the substituent $C_{3-x}$ cycloalkyl-O— containing from 3 to x carbon atoms.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl ring system.

The term "$C_{7-16}$ aralkyl" as used herein, either alone or in combination with another substituent, means an aryl as defined above linked through an alkyl group, wherein alkyl is as defined above containing from 1 to 6 carbon atoms. Aralkyl includes for example benzyl, and butylphenyl.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

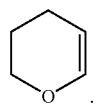

The term "Het" also includes a heterocycle as defined above fused to one or more other cycle be it a heterocycle or a carbocycle, each of which may be saturated or unsaturated. One such example includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic "heteroaryl" systems include: quinoline, indole, pyridine,

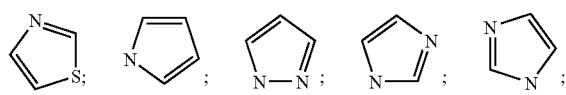

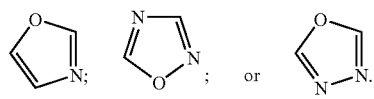

The term "oxo" means the double-bonded group (═O) attached as a substituent.

The term "thio" means the double-bonded group (═S) attached as a substituent.

In general, all tautomeric forms and isomeric forms and mixtures, whether individual geometric isomers, stereoisomers, optical isomers or racemic or non-racemic mixtures of isomers, of a chemical structure or compound are intended, unless the specific stereochemistry or isomeric form is specifically indicated in the compound name or structure.

The term "pharmaceutically acceptable ester" as used herein, either alone or in combination with another substituent, means esters of the compound of formula I in which any of the carboxylic acid functions of the molecule, but preferably the carboxy terminus, is replaced by an alkoxycarbonyl function:

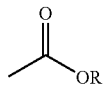

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in *Design of Prodrugs*, Bundgaard, H. Ed. Elsevier (1985) incorporated herewith by reference. Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see *Pharmaceutical Salts*, Birge, S. M. et al., J. Pharm. Sci., (1977), 66, 1-19, incorporated herein by reference).

Embodiments of the Invention

In the synthetic schemes below, unless specified otherwise, all the substituent groups in the chemical formulas shall have the same meanings as in the Formula (I). The reactants used in the synthetic schemes described below, including the diene compounds of formula III, may be obtained either as described herein, or if not described herein, are themselves either commercially available or may be prepared from commercially available materials by methods known in the art. Certain starting materials, for example, may be obtained by methods described in the International Patent Applications WO 00/09543 and WO 00/09558, U.S. Pat. No. 6,323,180 B1, U.S. Pat. No. 6,608,027 B1 and U.S. Application Publication Nos. 2003/0224977 A1, 2005/0080005 A1 and 2005/0049187 A1.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

In one general embodiment, the present invention is directed to a process for preparing a compound of formula I, said process comprising the protection of the compound of formula III to obtain the compound of formula IV wherein $PG_N$ is a suitable nitrogen protecting group, ring-closing the resulting compound of formula IV by cyclizing it in the presence of a suitable catalyst in a suitable organic solvent to obtain the compound of formula V, and then deprotecting the resulting compound of formula V to obtain the compound of formula I, as outlined in the following Scheme I:

Scheme I

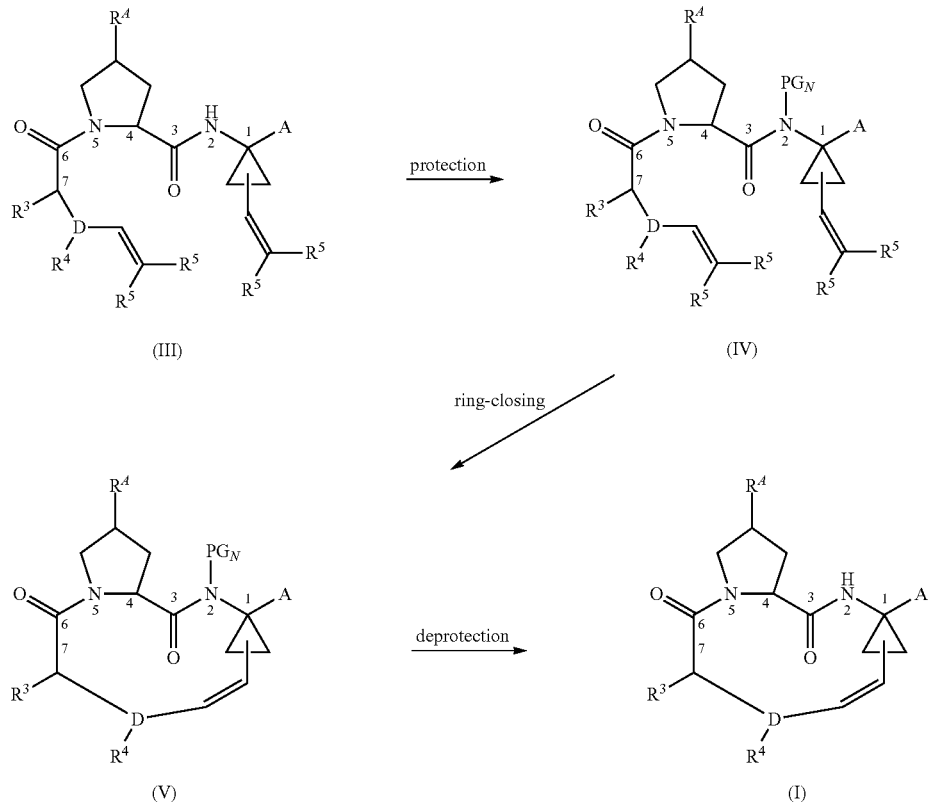

wherein the variable groups $R^A$, $R^3$, $R^4$, D and A are as defined previously, each $R^5$ is independently selected from H, $C_{1-6}$alkyl and $C_{3-6}$cycloalkyl and $PG_N$ is a suitable nitrogen protecting group.

The present invention is directed to the multi-step process depicted in Scheme I, as well as the individual reaction steps and the intermediates (IV) and (V). The details of the individual reaction steps will be described below.

Step 1—Conversion of III to IV

In Step 1, the secondary amide nitrogen atom in the diene compound of formula III is protected to obtain a compound of formula IV wherein $PG_N$ is a suitable nitrogen protecting group:

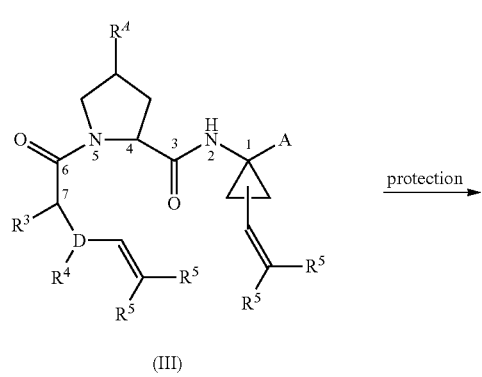

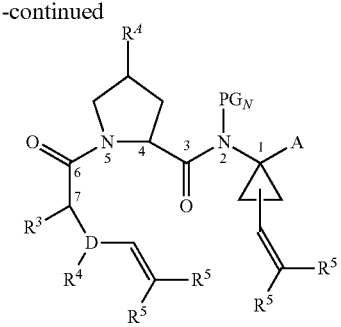

Each $R^5$ in formula (III) is independently selected from H, $C_{1-6}$alkyl and $C_{3-6}$cycloalkyl, preferably H.

The secondary amide nitrogen atom in the compound of formula III may be protected with any well-known nitrogen protecting group ($PG_N$) suitable for the process of the present invention, including, but not limited to the following: $C_{1-6}$alkyl, $C_6$ or $C_{10}$ aryl, $C_{7-16}$ aralkyl, —$COOC_{1-6}$alkyl, —$COC_{1-6}$alkyl, tri-$C_{1-6}$alkylsilyl, and phosphinamides, wherein any of the alkyl, aryl and aralkyl groups may be optionally substituted with one or more substitutents selected independently from: hydroxy, $C_{1-3}$alkoxy and tri-$C_{1-6}$alkyl-siloxy. The preferred choices for $PG_N$ are those groups that can be easily cleaved by acid or base hydrolysis, such as t-Boc (—COOt-Bu) or DMb (—$CH_2$—$C_6H_3(OCH_3)_2$).

This protection step is performed using any of the conventional nitrogen-protection protocols and conditions well known in the art for the particular nitrogen protecting group desired. Suitable procedures may be found, for example, in Greene et al., *Protective Groups in Organic Synthesis*, 3$^{rd}$ edition (1999) (published by John Wiley & Sons, Inc.), Chapter 7. When t-Boc is the desired nitrogen protecting group, for example, treatment of the corresponding unsubstituted diene compound (III) with Boc$_2$O and a catalytic amount of Dimethylaminopyridine (DMAP) gives the desired t-Boc-protected product. Suitable protection procedures may also be found in the Synthetic Examples section herein.

Step 2—Conversion of IV to V

In the next step, the compound of formula IV is cyclized in the presence of a suitable catalyst in a suitable organic solvent to obtain macrocyclic compound V:

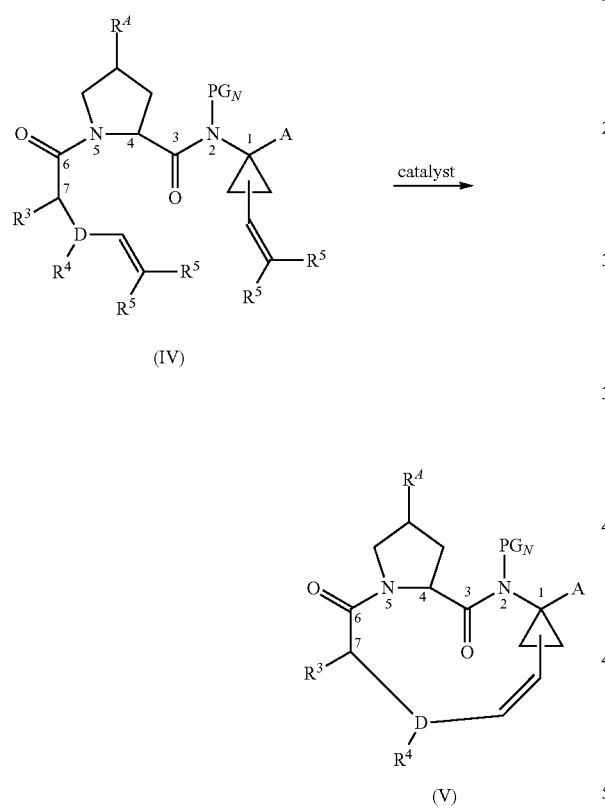

Suitable ring-closing catalysts for this cyclization step include ruthenium based catalysts, as well as the commonly used molybdenum-based (Schrock and modified Schrock catalysts) and tungsten-based catalysts. For example, any of the well-known ruthenium based catalysts used in olefin metathesis reactions, such as Grubb's catalyst (first and second generation), Hoveyda's catalyst (first and second generation) and Nolan's catalyst, may be used with appropriate adjustment of reaction conditions as may be necessary to allow ring-closing to proceed, depending upon the particular catalyst this is selected.

Suitable ruthenium catalysts for the metathesis cyclization step include any of the well-known ruthenium catalysts useful for RCM reactions, including the compounds of formula A, B, C, D or E:

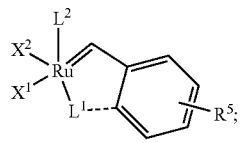
(A)

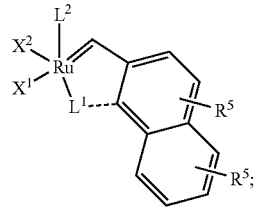
(B)

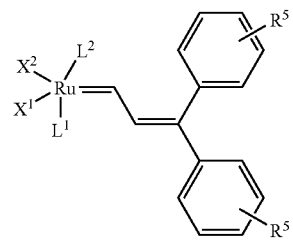
(C)

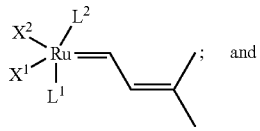
(D)

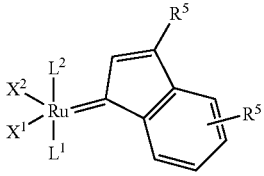
(E)

wherein $X^1$ and $X^2$ each independently represent an anionic ligand, $L^1$ represents a neutral electron donor ligand which is bonded to the ruthenium atom and is optionally bonded to the phenyl group, and $L^2$ represents a neutral electron donor ligand which is bonded to the ruthenium atom;

and $R^5$ is selected from one or more substituents on the benzene ring, each substituent independently selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl; and wherein $X^2$ and $L^2$ may optionally together form a chelating bidentate ligand.

In another embodiment the ruthenium catalyst is selected from A-1 and A-2:

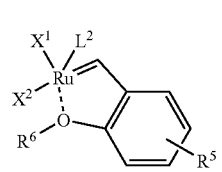
(A-1)

-continued

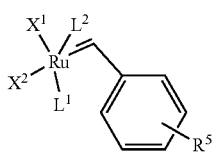
(A-2)

wherein:
L¹ is a trisubstituted phosphine group of the formula $PR_3$, wherein R is selected from $C_{1-6}$alkyl and $C_{3-8}$cycloalkyl,
L² is a trisubstituted phosphine group of the formula $PR_3$, wherein R is selected from $C_{1-6}$alkyl and $C_{3-8}$cycloalkyl,
or L² is a group of the formula A or B:

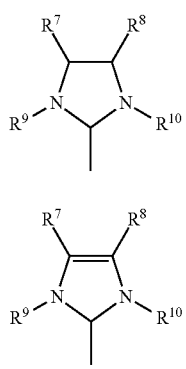

wherein
R⁷ and R⁸ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group; and R⁹ and R¹⁰ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group, each optionally substituted by one, two or three groups selected from hydrogen, $C_{1-6}$alkyl, halo$C_{1-6}$alkyl, HS—$C_{1-6}$ alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl;

X¹ and X² each independently represent a halogen atom;

R⁵ represent hydrogen or nitro; and

R⁶ represents a $C_{1-6}$ alkyl group.

In another embodiment the ruthenium catalyst is selected from:

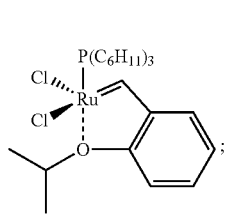 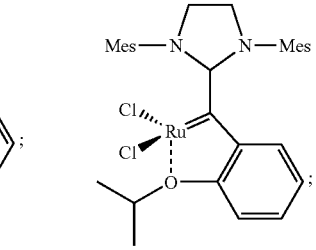

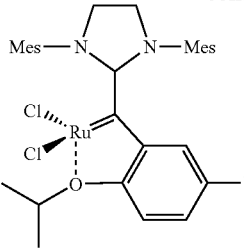 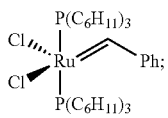

(Grela's catalyst)

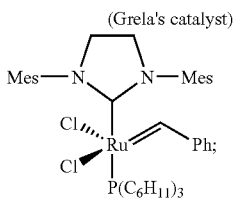 and 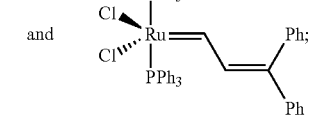

where Ph is phenyl and Mes is 2,4,6-trimethylphenyl.

Ruthenium-based catalysts useful for the metathesis cyclization step, such as those set forth above, are all known catalysts that may be obtained by known synthetic techniques. For example, see the references cited in the Background section above as well as the following references for examples of such ruthenium-based catalysts:

*Organometallics* 2002, 21, 671; 1999, 18, 5416; and 1998, 17, 2758;

*J. Am. Chem. Soc.* 2001, 123, 6543; 1999, 121, 791; 1999, 121, 2674; 2002, 124, 4954; 1998, 120, 2484; 1997, 119, 3887; 1996, 118, 100; and 1996, 118, 9606

*J. Org. Chem.* 1998, 63, 9904; and 1999, 64, 7202;

*Angew. Chem. Int. Ed. Engl.* 1998, 37, 2685; 1995, 34, 2038; 2000, 39, 3012 and 2002, 41, 4038;

U.S. Pat. Nos. 5,811,515; 6,306,987 B1; and 6,608,027 B1

The relative concentration levels of the substrate of formula IV and the catalyst, as well as the other processing conditions, can be readily adjusted by a person skilled in the art to obtain optimum results for any particular process.

In another specific embodiment of the present invention the ring-closing reaction is carried out in a solvent at a temperature in the range of from about 20° to about 120° C. Any solvent that is suitable for the ring closing metathesis reaction may be used. Examples of suitable solvents include alkanes, such as n-pentane, n-hexane or n-heptane, aromatic hydrocarbons, such as benzene, toluene or xylene, chlorinated hydrocarbons such as dichloromethane, trichloromethane, tetrachloromethane or dichloroethane, tetrahydrofuran, 2-methyl-tetrahydrofuran, 3-methyl-tetrahydrofuran, cyclopentyl methyl ether, methyl tert-butyl ether, dimethyl ether, methyl alcohol, dioxane, ethyl acetate and tert-butyl acetate.

In another specific embodiment of the present invention the ring-closing reaction is carried out wherein the molar ratio of the diene compound (IV) to the catalyst ranges from 1000:1 to 100:1, preferably from 1000:1 to 250:1, in particular from 700:1 to 330:1.

In another specific embodiment of the present invention the ring-closing reaction is carried out at a ratio of the diene compound (IV) to solvent in the range from 1:200 by weight to 1:4 by weight, preferably from 1:50 by weight to 1:7 by weight, in particular from 1:14 by weight to 1:7 by weight.

In another specific embodiment of the present invention the ring-closing reaction is carried out by continuous addition of the catalyst solution in an appropriate solvent such as toluene or dichloromethane within a reasonable time frame, preferably 30 min to 2 h.

One skilled in the art can readily optimize the cyclization step by selecting and adjusting appropriate conditions suitable for the particular ring-closing catalyst selected. For example, depending upon the catalyst selected it may be preferable to run the cyclization step at high temperature, e.g., higher than 90° C., although lower temperatures may also be possible with the addition of an activator such as copper halide (CuX, where X is halogen) to the reaction mixture.

In a particular embodiment of this step, the compound of formula (IV) is dissolved in a degassed organic solvent (such as toluene or dichloromethane) to a concentration below about 0.02M, then treated with a ruthenium-based catalyst such as Grela's catalyst, at a temperature from about 40° C. to about 110° C. until completion of the reaction. Some or all of the ruthenium metal may be removed from the reaction mixture by treatment with a suitable heavy metal scavenger, such as THP, imidazole, or other agents known to scavenge heavy metals. The reaction mixture is then washed with water and the organic layer separated and washed. The resulting organic solution may be decolorized, such as by the addition of activated charcoal with subsequent filtration.

In one embodiment, the proline ring oxygen atom in formula (IV) has been protected with a protecting group (where $R^A$=O-PG) at any time prior to the cyclization step using conventional techniques. Any suitable oxygen protecting group may be used including, for example, acetate, benzyloxy, benzoate, para-nitro benzoate, naphthoates, halogenoacetate, methoxyacetate, phenyl acetate, phenoxy acetate, pivaloate, crotonate, methyl carbonate, methoxymethyl carbonate, ethyl carbonate, halogeno carbonate, para-nitro phenyl carbonate, triisopropyl silyl, triethyl silyl, dimethylisopropyl, diethylisopropyl, dimethylthexylsilyl, t-butyldimethylsilyl, t-butyldiphenylsilyl, tribenzylsilyl, triphenylsilyl, diphenylmethylsilyl, di-t-butylmethylsilyl, tris(trimethylsilyl)silyl, t-butoxymethoxyphenylsilyl, t-butoxydiphenylsilyl, etc.

Additionally, any other amine or carboxylic acid groups that might be present in the diene compound of formula (IV) may be protected with appropriate protecting groups at any time prior to the cyclization step using conventional protecting groups and techniques well known in the art. Locations where additional protecting groups may be desired include, for example. in the $R^3$ moiety (amine protection) or in the A moiety (carboxylic acid protection). The amine groups can be protected with conventional nitrogen protecting groups, such as t-Boc, and the carboxylic acid groups can be protected with conventional carboxylic acid protecting groups, such as alkyl esters, alkyl amides and nitrile groups.

In another embodiment, it may be desirable to purify the solution of diene compound of formula (III) prior to the methathesis cyclization step to remove any impurities from the reaction mixture that might inhibit the cyclization reaction. Conventional purification procedures well known to those skilled in this art may be employed. In one embodiment, the solution of diene compound may be purified by treatment with alumina, for example, activated alumina, prior to its use in the cyclization step. In another embodiment, the diene compound was purified by recrystallization from an appropriate solvent system, with either single solvent or solvent mixtures containing more than one solvent.

Step 3—Conversion of V to I

In this step, the compound of formula V is subjected to deprotection conditions to remove the nitrogen protecting group $PG_N$ to obtain the compound of formula I:

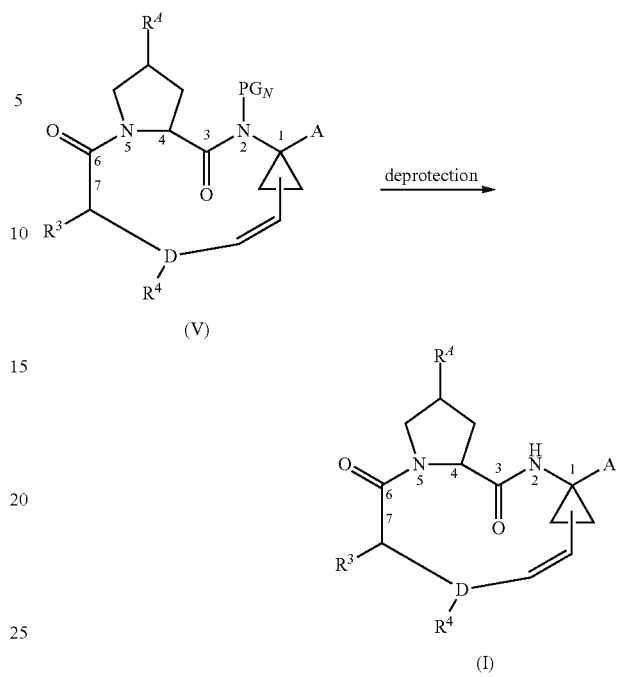

This deprotection step is performed using any of the conventional deprotection protocols well known in the art for removing the nitrogen protecting group. Suitable procedures may be found, for example, in Greene et al., *Protective Groups in Organic Synthesis*, 3$^{rd}$ edition (1999) (published by John Wiley & Sons, Inc.), Chapter 7. For example, a t-Boc nitrogen protecting group on compound (V) can be removed by treating compound (V) with an acid. Suitable acids include hydrochloric acid, hydrobromic acid, benzenesulfonic acid, toluenesulfonic acid, and trifluoroacetic acid.

Depending on the particular post-ring-closing steps that may be planned for the product of formula (I), it might also be desirable to remove any additional protecting groups that may be present in the cyclized product, e.g., when $R^A$ is a protected hydroxyl (O-PG) group, when A is a protected carboxylic acid group, or when $R^3$ contains an amino protecting group. The removal of these other protecting groups that might be present in compound (V) can take place at any time subsequent to the ring-closing step, i.e., prior to, during, or subsequent to the removal of the $PG_N$ group (in Step 3), or even later on during downstream processing of compound (I). The removal of such other protecting groups can be performed using any of the conventional deprotection protocols well known in the art for removing the particular protecting group. For example, a protocol for simultaneously removing the t-Boc nitrogen protecting group, an acetyl oxygen protecting group and a methyl-ester protecting group on the carboxylic acid can be found in the Synthetic Examples section below.

Additional Embodiments of Formulae IV, V and I

In a specific embodiment of the process, a compound of formula I is prepared wherein:
$R^A$ is selected from: OH, O-PG, where PG is a protecting group, or —OSO$_2$—R$^{27}$, wherein R$^{27}$ is selected from p-tolyl, p-bromophenyl, p-nitrophenyl, methyl, trifluoromethyl, perfluorobutyl and 2,2,2-trifluoroethyl;
or $R^A$ is a group of formula II:

(II)

[Structure of formula (II): a quinoline-like ring with substituents L⁰, L¹, L², W, R²², and an O- group at position 4]

wherein:
W is N;
L⁰ is H, $C_{1-6}$ alkyl, $C_{1-6}$ alkoxy, hydroxy, chloro;
L¹ and L² are each independently H, halogen or $C_{1-4}$alkyl;
R²² is H, $C_{1-6}$ thioalkyl, $C_{1-6}$ alkoxy, phenyl or Het selected from the group consisting of:

[Structures of various heterocycles bearing R²⁴ substituents: thiazole, thiazole isomer, pyrrole, pyrazole, imidazole, imidazole isomer, oxazole, oxadiazole, oxadiazole isomer, pyridine, and dihydropyran]

wherein R²⁴ is H, $C_{1-6}$ alkyl, NH—$R^{25}$, NH—C(O)—$R^{25}$; NH—C(O)—NH—$R^{25}$,
wherein each $R^{25}$ is independently: H, $C_{1-6}$ alkyl, or $C_{3-6}$ cycloalkyl;
or NH—C(O)—$OR^{26}$, wherein $R^{26}$ is $C_{1-6}$ alkyl; or
R³ is N(R*)—C(O)—$OR^{20}$, wherein R* is H or a protecting group and $R^{20}$ is $C_{1-6}$ alkyl, or $C_{3-6}$ cycloalkyl;
D is a 4 to 6 atom saturated alkylene chain optionally containing one or two heteroatoms independently selected from: O, S or N—$R^{27}$, wherein $R^{27}$ is H, $C_{1-6}$alkyl or $C_{2-7}$acyl;
R⁴ is H or $C_{1-6}$ alkyl;
and A is a carboxylic acid or a pharmaceutically acceptable salt or ester thereof.

In another specific embodiment of the process, a compound of formula I is prepared wherein:
$R^A$ is selected from: OH, O-PG, where PG is a protecting group, or —OSO₂—$R^{27}$, wherein $R^{27}$ is selected from p-tolyl, p-bromophenyl, p-nitrophenyl, methyl, trifluoromethyl, perfluorobutyl and 2,2,2-trifluoroethyl;
R³ is N(R*)—C(O)—$OR^{20}$, wherein $R^{20}$ is butyl, cyclobutyl or cyclopentyl; and R* is H or a protecting group;
R⁴ is H or $C_{1-6}$ alkyl;
D is a 5 atom saturated alkylene chain; and
A is a carboxylic acid or a pharmaceutically acceptable salt or ester thereof.

In another specific embodiment of the process, a compound of formula I is prepared wherein:

$R^A$ is selected from: OH, p-nitrobenzoyloxy, t-butyldimethylsilyloxy, acetyloxy, and —OSO₂—$R^{27}$, wherein $R^{27}$ is p-bromophenyl;
R³ is N(R*)—C(O)—$OR^{20}$, wherein $R^{20}$ is cyclopentyl; and R* is H or a protecting group;
R⁴ is H or $C_{1-3}$ alkyl;
D is a 5 atom saturated alkylene chain; and
A is a carboxylic acid or a pharmaceutically acceptable salt or ester thereof.

Specific examples of the compounds of formula (I) that may be prepared by the process of the present invention may be found in the Synthetic Examples section below and also in U.S. Pat. No. 6,608,027 B1 and in U.S. Application Publication Nos. 2003/0224977 A1, 2005/0080005 A1 and 2005/0049187 A1.

Specific embodiments of the intermediate compounds of formulae (IV) and (V) that may be prepared and used in the process of the present invention include those corresponding to the various specific embodiments of formula (I) set forth above, but having a nitrogen protecting group ($PG_N$) on the secondary amide nitrogen atom. A preferred $PG_N$ group is —COO$C_{1-6}$alkyl, more preferably tert-butyloxycarbonyl (t-Boc). A preferred R⁵ group in formula (IV) is hydrogen.

Preparation of Starting Materials

The diene compounds of formula (III) used as a starting material may be obtained from commercially available materials using conventional techniques described in the art. See, for example, U.S. Pat. No. 6,608,027 B1 and U.S. Application Publication Nos. 2003/0224977 A1, 2005/0080005 A1 and 2005/0049187 A1.

The following reaction sequence provides yet another alternative method to prepare certain intermediate compounds of formula III where $R^A$ is a group of formula II (i.e., the compounds of formula IIIA):

(i) reacting a compound of the formula (2) with a compound of the formula (3) to obtain a compound of the formula (4):

[Structure: pyrrolidine with OH at 4-position, N-PG, and COOH at 2-position]
(2)

+

[Structure: quinoline ring with L⁰, L¹, L², W, R²², and X substituents]
(3)

→

[Structure: pyrrolidine with O-Q at 4-position, N-PG, and COOH at 2-position]
(4)

wherein PG is an amino protecting group, X is a halogen atom and Q is a substituent of the following formula:

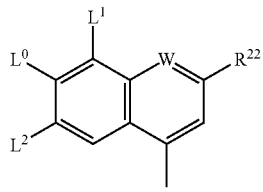

(ii) reacting a compound of the formula (4) with a compound of the formula (5) to obtain a compound of the formula (6):

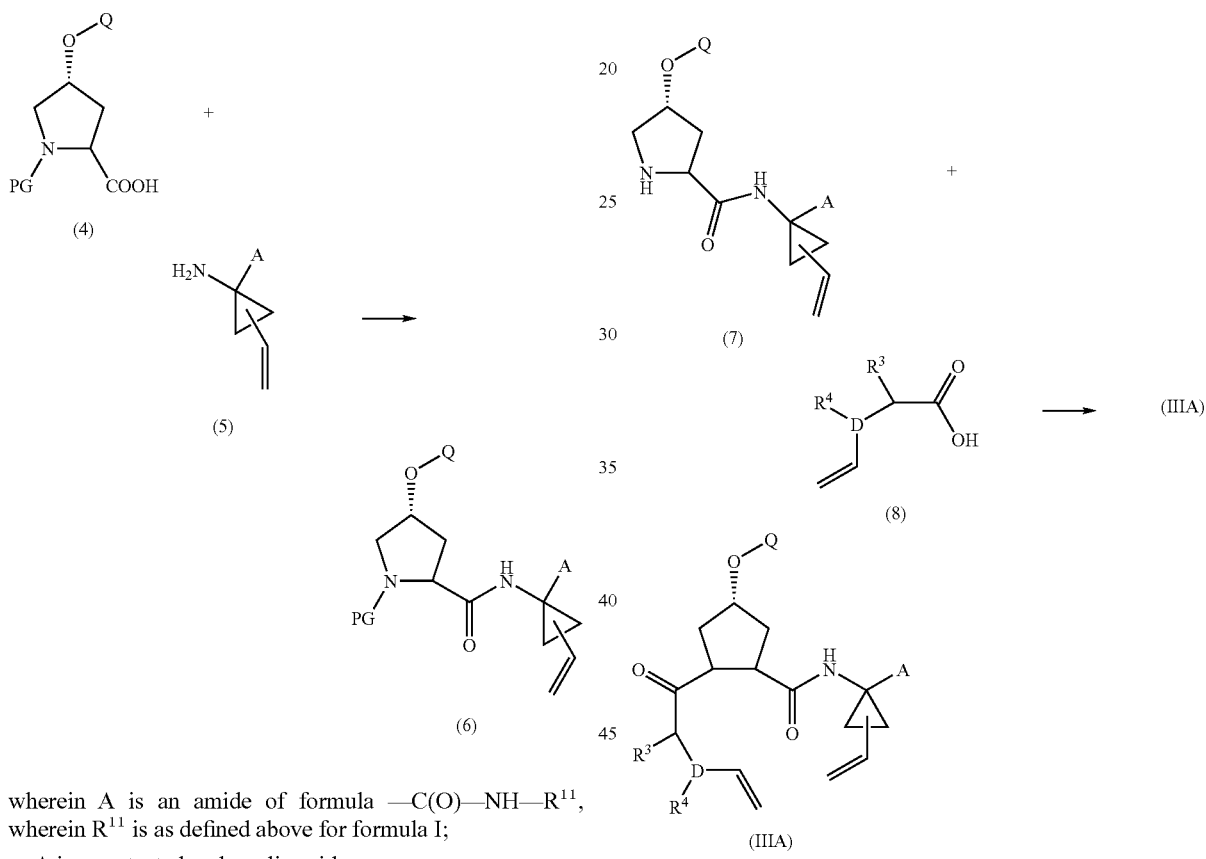

wherein A is an amide of formula —C(O)—NH—R$^{11}$, wherein R$^{11}$ is as defined above for formula I;
or A is a protected carboxylic acid group;

(iii) removing the nitrogen protecting group in the compound of formula (6) to obtain a compound of the formula (7):

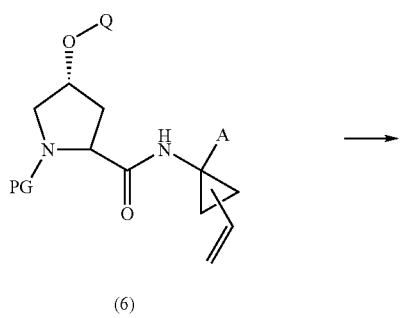

(iv) reacting a compound of the formula (7) with a compound of the formula (8) to obtain a compound of the formula (IIIA):

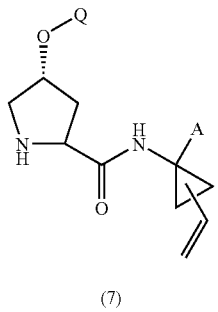

Step (i)

The coupling reaction between the compounds of formulas (2) and (3) is typically preformed in the presence of a base in a suitable solvent. Examples of suitable bases for this reaction include t-BuOK, t-BuONa, sodium bis(trimethylsilyl)amide, KDMO, with t-BuOK being a preferred base. Examples of suitable solvents for this reaction include polar aprotic solvents, for example, DMSO, DMF, NMP or other common polar aprotic solvents.

The amino-protecting group PG can be any suitable amino-protecting group that is well known in the art. See, e.g. those described in WO 00/09543, WO 00/09558. Typical examples of protecting groups that may be used are carbamate protecting groups such as Boc, or CBZ groups.

The X group in formula (3) is any halogen atom, but preferred is chlorine.

The compounds of formula (2) used as starting material are either commercially available, e.g., Boc-4(R)-hydroxyproline, or can be prepared from known materials using conventional techniques. In one example, the compounds of formula (2) may be prepared by amino-protection of the 4-hydroxyproline compounds of formula (X):

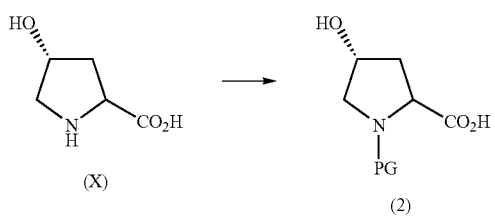

In the first step, an appropriate amino-protecting group is introduced onto the ring nitrogen atom of the 4-hydroxyproline compound of formula (X) using conventional procedures. For example, the compound of formula (X) may be dissolved in a suitable solvent and reacted with an appropriate amino-protecting group introducing reagent. For example, and not intending to be limited in its scope, when Boc (tert-butyloxycarbonyl) is the desired protecting group, compound (X) is reacted with the anhydride $Boc_2O$ (or Boc-ON) in a solvent mixture such as Acetone/Water, MIBK/Water or THF/Water to which a base such as NaOH, KOH, LiOH, triethylamine, diisopropylethylamine, or N-methyl-pyrrolidine is added, the reaction being carried out at a temperature between 20-60° C.

The halogen-substituted quinoline compounds of formula (3) can be prepared from the corresponding hydroxyl-substituted quinoline compounds of the following formula (3') by following well known halogenation procedures using various halogenation reagents under a variety of conditions known in the art. Examples of such reagents include the commonly used $POX_3$ and $PX_5$, where X=F, Cl, Br or I, wherein these reagents can be used in some cases as solvents or in combination with polar aprotic solvents, such as DMF or Acetonitrile.

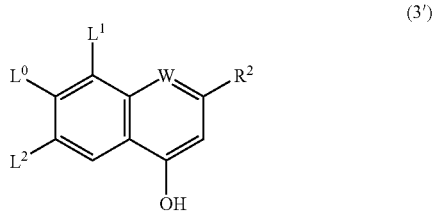

For examples of halogenation conditions that may be employed, see:

Chlorination: Outt, P. E. et al, *J Org Chem* 1998, 63 (17), 5762-5768 and references therein;

Bromination: Nakahara, S. et al, *Tetrahedron Lett* 1998, 39 (31), 5521-5522 and references therein Additional solvent: Nomoto, Y.; et al, *Chem Pharm Bull* 1990, 38 (8), 2179-2183.

The hydroxyl-substituted quinoline compounds of formula (3') can be synthesized from commercially available materials using the techniques described in WO 00/59929, WO 00/09543 and WO 00/09558, U.S. Pat. No. 6,323,180 B1, U.S. Pat. No. 6,608,027 B1 and U.S. Patent Application Publication No. 2005/0020503 A1.

Step (ii)

In this step, the compounds of formulas (4) and (5) may be linked together by well known peptide coupling techniques. See, for example, the techniques disclosed in WO 00/09543, WO 00/09558 and U.S. Pat. No. 6,608,027 B1. Peptide coupling between compounds of formula (4) and (5) could be obtained, for example, under a variety of conditions known in the art using conventional peptide coupling reagents such as DCC, EDC, TBTU, HBTU, HATU, DMTMM, HOBT, or HOAT in aprotic solvents such as dichloromethane, chloroform, THF, DMF, NMP, DMSO.

The compounds of formula (5) are known from WO 00/09543, WO 00/09558 and U.S. Pat. No. 6,608,027 B1, and may be prepared by techniques as described therein.

Step (iii)

This step of cleaving the nitrogen protecting group in the compound of formula (6) can also be accomplished by well known techniques, e.g., as described in 00/09543, WO 00/09558 and U.S. Pat. No. 6,608,027 B1. In particular embodiments, this process involves the acid hydrolysis of the compound of formula (6) with an organic or inorganic acid, such as HCl, $H_2SO_4$, TFA, AcOH, $MeSO_3H$, $PhSO_3H$, TsOH in a variety of protic or nonprotic solvents such as alcohols, ethers, toluene, ACN or DCM.

Step (iv)

In this step, the compounds of formulas (7) and (8) may be linked together by the same well known peptide coupling techniques as described above in step (ii) for the peptide coupling of formulas (4) and (5). Exemplary conditions are the same as described above for step (ii).

The substituted acid compound of formula (8) used as a starting material are known from U.S. Pat. No. 6,608,027 B1 and may be obtained from commercially available materials using the techniques as described therein.

Post Processing Steps

After the reaction steps leading to the macrocyclic compounds of formula (I), additional reaction steps are possible leading to other compounds of formula (I). For example, when $R^4$ is OH, O-PG, where PG is a protecting group, or $-OSO_2-R^{27}$ in formula (I), such compounds can be converted to other compounds of formula (I) wherein $R^4$ is a group of formula (II) by the procedures fully disclosed in U.S. Pat. No. 6,608,027 B1 and U.S. Application Publication Nos. 2003/0224977 A1, 2005/0080005 A1 and 2005/0049187 A1. As fully described in these patent references, for example, the compounds of formula (I) wherein $R^4$ is OH or $-OSO_2-R^{27}$ can be reacted with a compound of formula (VI) to obtain a compound of formula (I) wherein $R^4$ is a group of formula (II):

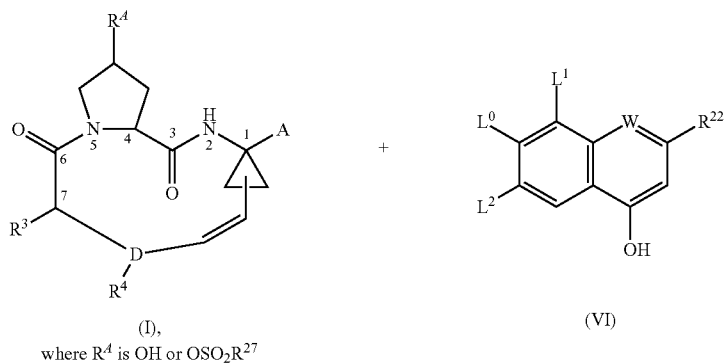
(I),
where $R^A$ is OH or $OSO_2R^{27}$
(VI)
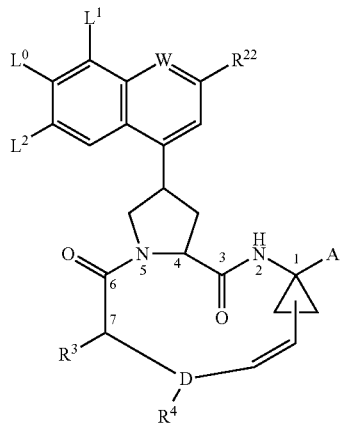
(I), where $R^A$ is formula II
In another embodiment, the compounds of formula (I) where $R^A$ is OH can be reacted with a sulfonated compound QUIN to obtain a compound of formula (I) wherein $R^A$ is a group of formula (II), as shown by the following reaction scheme:
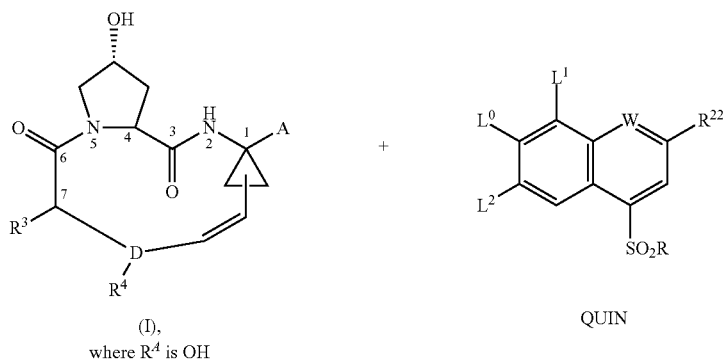
(I),
where $R^A$ is OH
QUIN

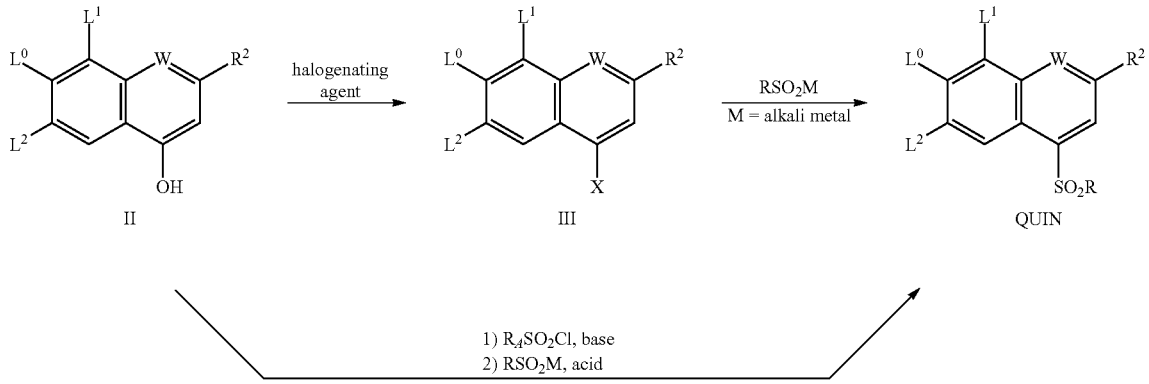

(I),
where $R^4$ is formula II

The R group on the sulfonyl group in QUIN include, for example, $C_{1-6}$alkyl, $C_6$ or $C_{10}$ aryl or heteroaryl. A preferred R group is phenyl.

The coupling reaction between the compounds of formulas (I) and QUIN is typically preformed in the presence of a base in a suitable solvent. Examples of suitable bases for this reaction include t-BuOK, t-BuONa, t-BuOCs, sodium bis(trimethylsilyl)amide, and KDMO, with t-BuOK and KDMO being preferred bases. Examples of suitable solvents for this reaction include polar aprotic solvents, for example, DMSO, DMF, NMP or other common polar aprotic solvents, as well as THF and other moderately polar ethers. A preferred solvent is DMSO.

The preferred temperature would be between 0° C. and 50° C. (depending upon solvent freezing points), and most preferably between 10° C. and 25° C.

In yet another preferred embodiment of this step, the following set of reaction conditions may be employed: A flask is charged with the macrocycle (I) and QUIN, purged with nitrogen (3 times), then DMSO is added via syringe. The mixture is again purged with nitrogen (3 times), and the temperature adjusted to 20° C. To the slurry is then added 50% KDMO/heptane via syringe pump over 1 hour. The resulting mixture is stirred under nitrogen at ~20° C. for 2 h. The mixture is then quenched by the dropwise addition of glacial HOAc, and the mixture is stirred. The reaction mixture is then slowly added to water, to cause product precipitation. The slurry is then stirred, filtered, and the cake washed with water, then hexanes, and the solid dried.

When A is a protected carboxylic acid group in formula (I), e.g. a carboxylic acid ester group, the compound of formula (I) can optionally be subjected to de-protection (hydrolysis) conditions to obtain the corresponding free carboxylic acid compound. Hydrolysis can be carried out using conventional hydrolysis conditions known in the art.

The sulfonated starting material QUIN can be prepared from known materials according to the procedure outlined in the Scheme II below:

Scheme II

These hydroxyl-substituted quinolines II can be converted to sulfonequinolines QUIN by first converting them to a haloquinoline compound III (where X is halogen) by following well known halogenation procedures using various halogenating reagents such as the commonly used $POX_3$ and $PX_5$, where X=F, Cl, Br or I, wherein these reagents can be used in some cases as solvents or in combination with polar aprotic solvents, such as DMF or Acetonitrile; and then converting halogenated compound III to the target sulfonequinoline QUIN by reaction with a sulfinate salt $RSO_2M$ wherein M is an alkali metal, such as $PhSO_2Na$.

Alternatively, II can be converted to the sulfonequinoline in a one-pot procedure by first generating an intermediate sulfonate by reaction with an arene sulfonylchloride compound $R_ASO_2Cl$ wherein $R_A$ is an electron rich arene group, such as benzenesulfonyl chloride or tosyl chloride, in the presence of a suitable base in a suitable solvent. Suitable bases for this step include tertiary amine bases such as N-methylpyrrolidine and diisopropylethylamine, and suitable solvents include aprotic solvents such as acetonitrile, THF, toluene and DMF, preferably acetonitrile. The resulting species is then reacted in situ, under acidic conditions (for example in the presence of acetic, trifluoroacetic, hydrochloric acid or the like, preferably acetic acid), with a sulfinate salt $RSO_2M$ wherein M is an alkali metal, such as $PhSO_2Na$ or $PhSO_2K$, at a suitable reaction temperature, for example in the range of 0 to 100° C., preferably 25 to 50° C. The sulfonequinoline product can be isolated from the reaction mixture using conventional techniques well know to those skilled in the art. In one embodiment, the sulfonequinoline can be crystallized out by cooling the solution to room temperature and adding water. The crystallized product can then be filtered, rinsed and washed using conventional techniques.

The hydroxyl-substituted quinoline compounds of formula (II) can be synthesized from commercially available materials using the techniques described in, e.g. from WO 00/59929, WO 00/09543 and WO 00/09558, U.S. Pat. No. 6,323,180 B1, U.S. Pat. No. 6,608,027 B1 and U.S. Application Publication No. 2005/0020503 A1.

SYNTHETIC EXAMPLES

Examples 1 to 7

Comparison of Ring-Closing Step Using Substituted and Non-Substituted Substrates The following examples are presented to demonstrate the improved results obtainable in the ring-closing step by using a nitrogen-substituted substrate according to the present invention vs. using an unsubstituted substrate. Higher yields are demonstrated across all examples, even with increased concentration of substrate.

Example 1 p-Nitrobenzoyl Substrates 1a and 1b

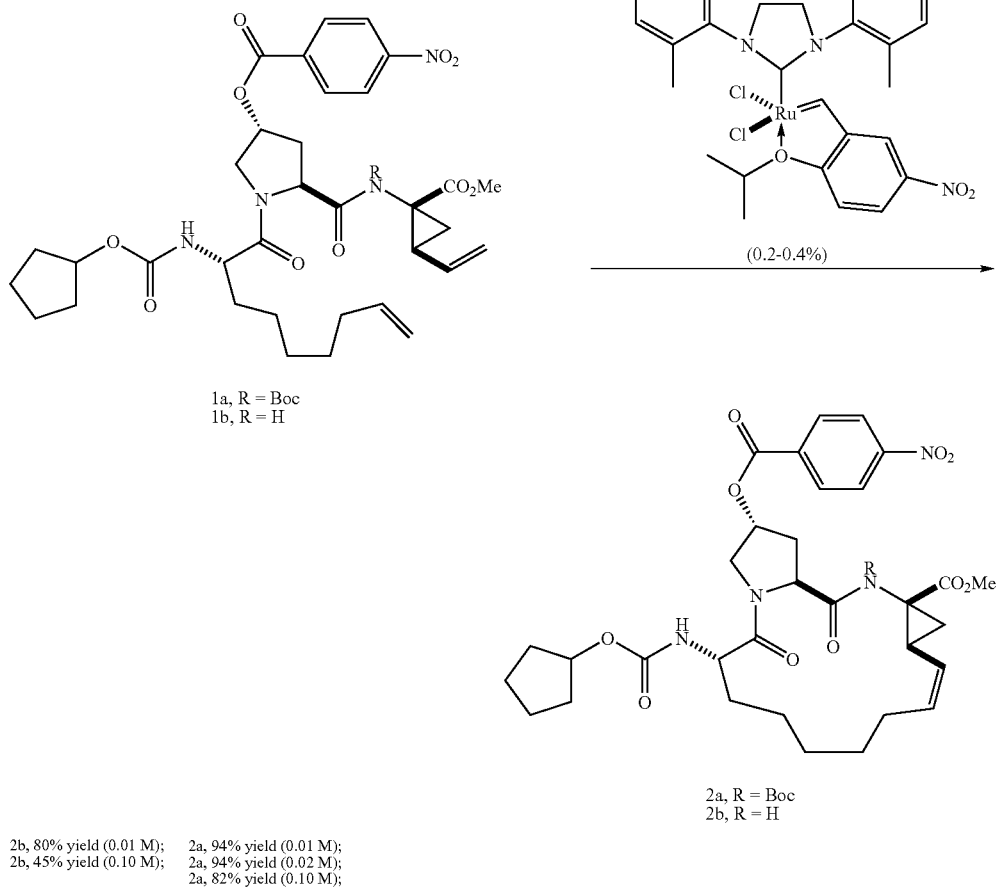

1a, R = Boc
1b, R = H

2a, R = Boc
2b, R = H 2b, 80% yield (0.01 M); 2a, 94% yield (0.01 M);
2b, 45% yield (0.10 M); 2a, 94% yield (0.02 M);
2a, 82% yield (0.10 M);

Example 2
t-Butyldimethylsilyl Substrates 1c and 1d
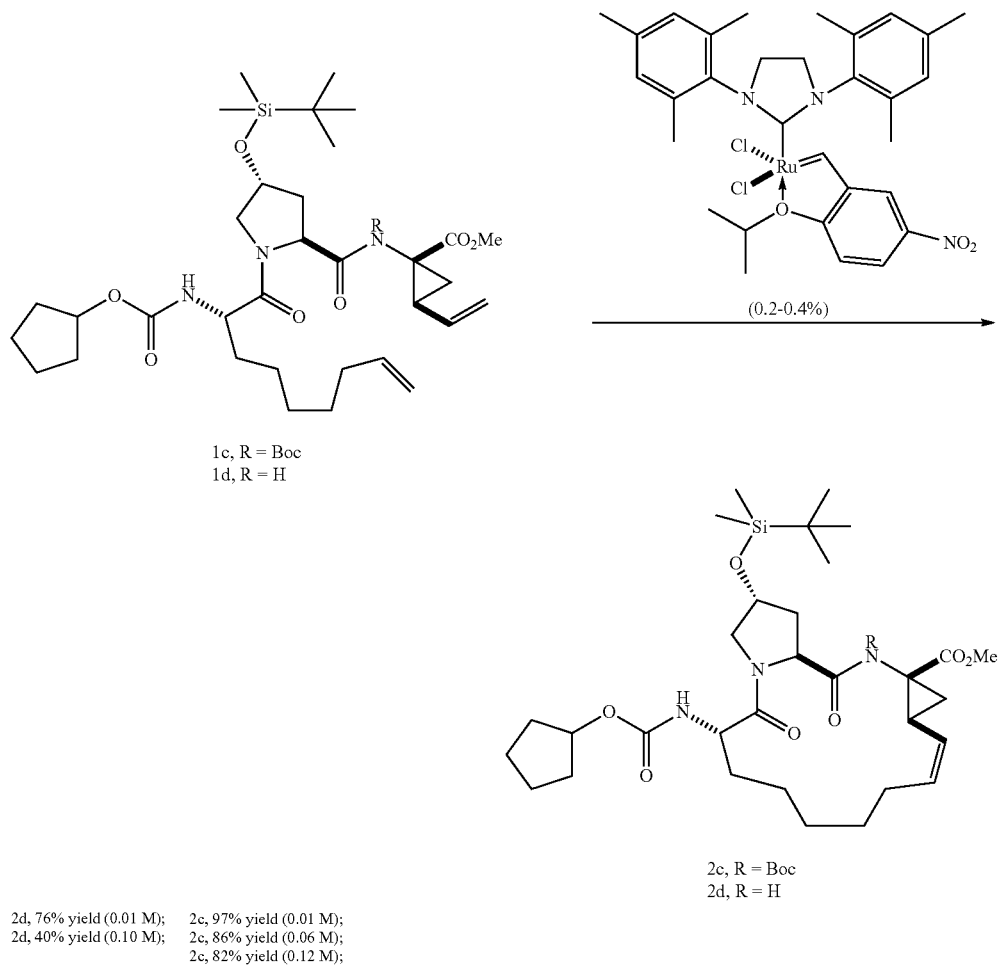
2d, 76% yield (0.01 M);   2c, 97% yield (0.01 M);
2d, 40% yield (0.10 M);   2c, 86% yield (0.06 M);
                          2c, 82% yield (0.12 M);
Example 3
Acetyl Substrates 1e and 1f
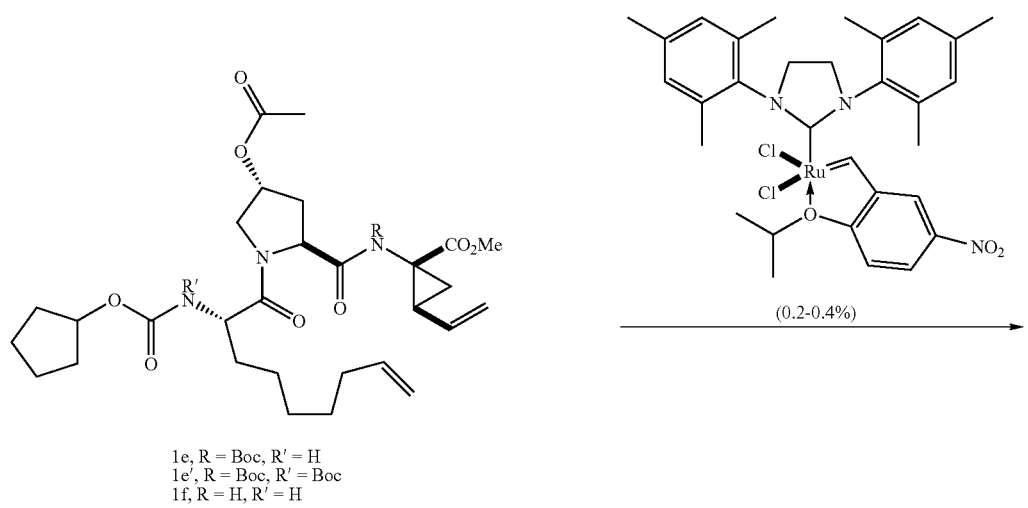

-continued
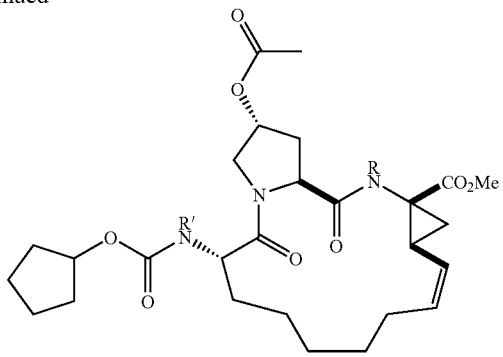
2e, R = Boc, R' = H
2e', R = Boc, R' = Boc
2f, R = H, R' = H
2f, 85% yield (0.01 M);  2e', 95% yield (0.01 M);  2e, 97% yield (0.01 M);
                        2e', 88% yield (0.10 M);  2e, 93% yield (0.10 M);
                                                  2e, 86% yield (0.20 M);
Example 4
Bromophenylsulfonyl Substrates 1g and 1h
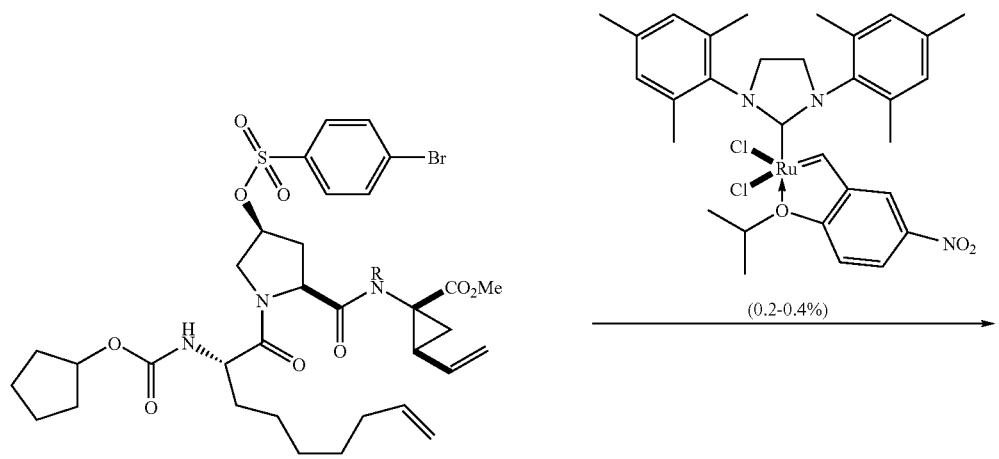
1g, R = Boc
1h, R = H
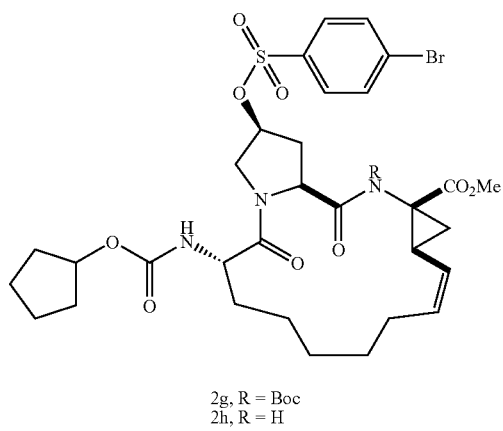
2g, R = Boc
2h, R = H
2h, 70% yield (0.01 M);  2g, 78% yield (0.10 M);

Example 5
Hydroxyl Substrates 1i and 1j
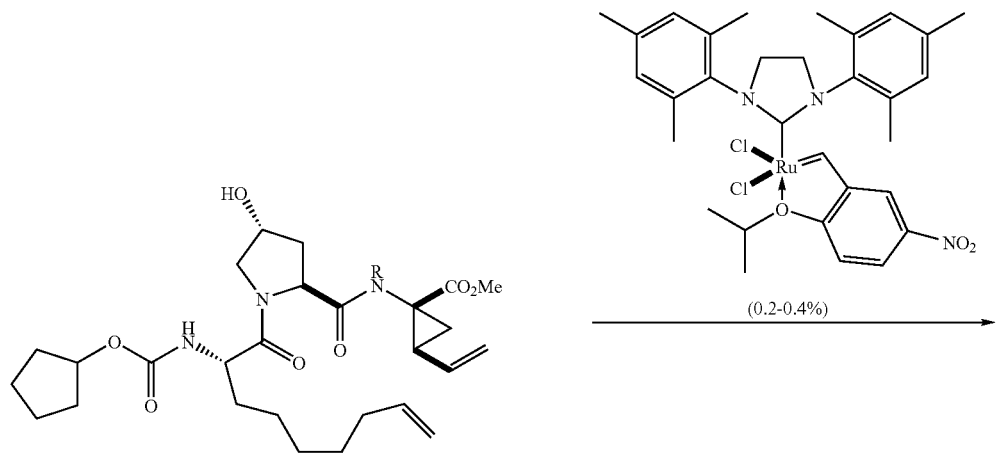
1i, R = Boc
1j, R = H
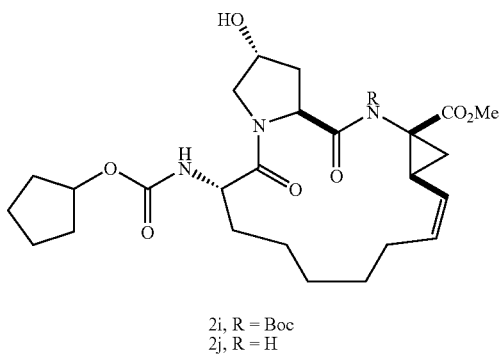
2i, R = Boc
2j, R = H
2j, 70% yield (0.01 M);    2j, 92% yield (0.01 M);
Example 6
Cis p-nitronitrobenzoyl substrates 1k and 1l
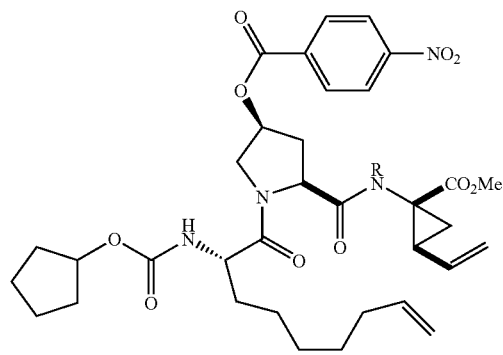
1k, R = Boc
1l, R = H
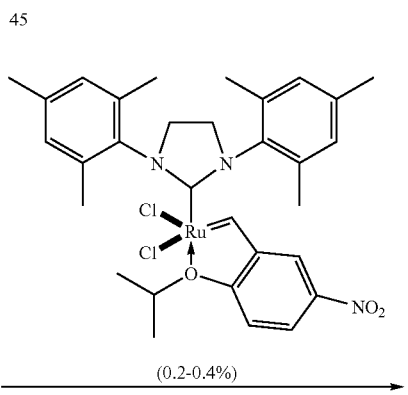

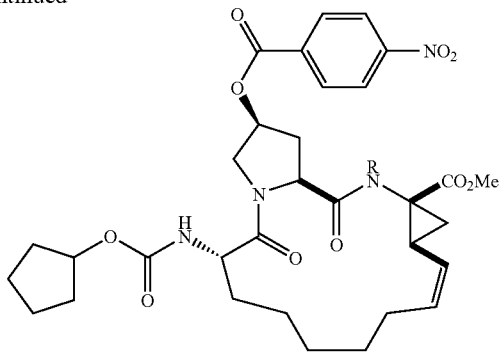
2k, R = Boc
2l, R = H
2l, 85% yield (0.01 M);   2k, 97% yield (0.01 M);
2l, 40% yield (0.10 M);   2k, 97% yield (0.05 M);
　　　　　　　　　　　　2k, 95% yield (0.10 M);
　　　　　　　　　　　　2k, 93% yield (0.20 M);
Example 7
Benzyl Substrates 1m and 1n
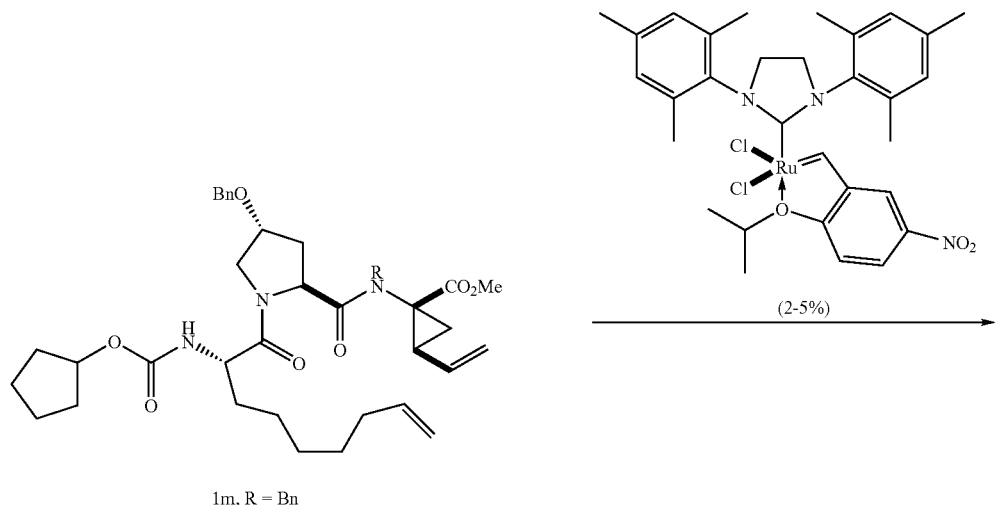
1m, R = Bn
1n, R = H
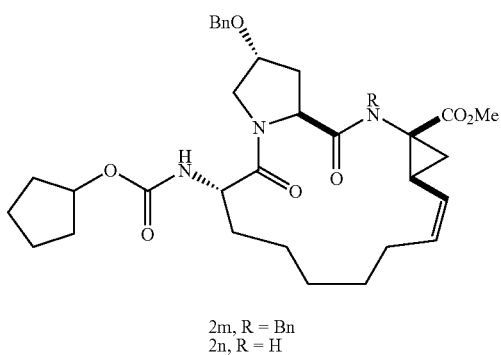
2m, R = Bn
2n, R = H
2n, 75% yield (0.01 M);   2m, 85% yield (0.01 M);

General Procedure for RCM Examples 1-7:

Diene (10 mmol, 1.0 eq) and an appropriate amount of toluene (corresponding to the desired diene concentration) were combined in a reaction vessel and degassed with $N_2$ for 30 min. The reaction was heated to 110° C. and the Ru catalyst (14 mg in 3 mL anhydrous toluene, 0.2%) was added over 15 min. After 15 min, a sample was taken and checked by HPLC. If the conversion was below 95%, additional Ru catalyst (14 mg in 3 mL anhydrous toluene per portion) was added until conversion reached 95%. For substrates 1m-1n, catalyst was added in portions of 1 mol % to reach full conversion. Imidazole (0.28 g, or 0.56 g if the $2^{nd}$ portion of Ru catalyst was added) was added and the reaction was stirred at 80° C. for 2 h and extracted with HCl (1 M in $H_2O$, 30 mL, or 60 mL if the $2^{nd}$ portion of Ru catalyst was added) and $H_2O$ (2×30 mL or 60 mL if the $2^{nd}$ portion of Ru catalyst was added). The organic phase was distilled to ~20 mL and circulated through a funnel (2 inch i.d.) of charcoal (4 g) and diatomaceous earth (1 g) three times. The solution was then concentrated and purified by column chromatography to give the desired macrocycle in the stated yield.

Example 8

Preparation of the Substrates Used in Examples 1 to 7

Preparation of Substrates 1a, 1c, 1e, 1g, 1i, 1k, 1m, and 1n

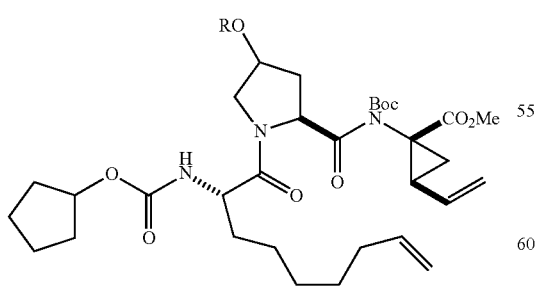

1b, 1d, 1f, 1h, 1l

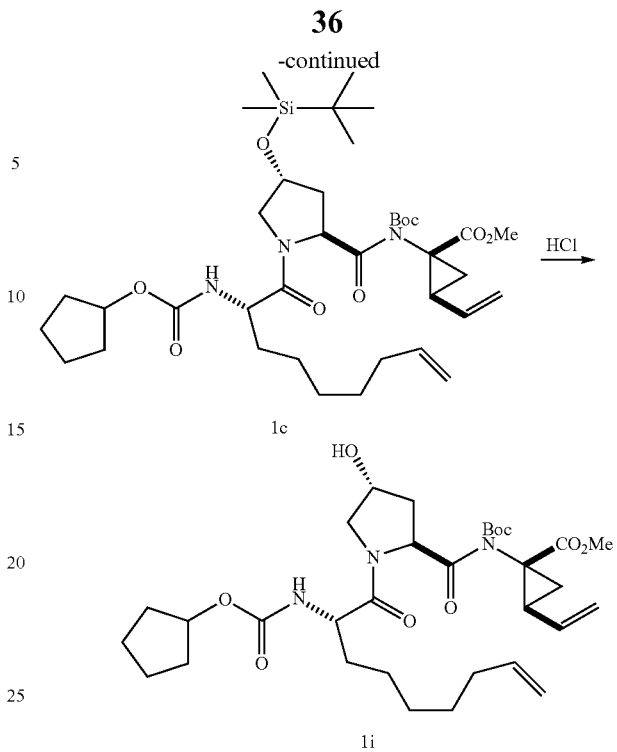

1a, 1c, 1e, 1g, 1k
1e': $Boc_2O$ (5 eq) and DMAP
(2 eq) were used
(52% yield from 1f)

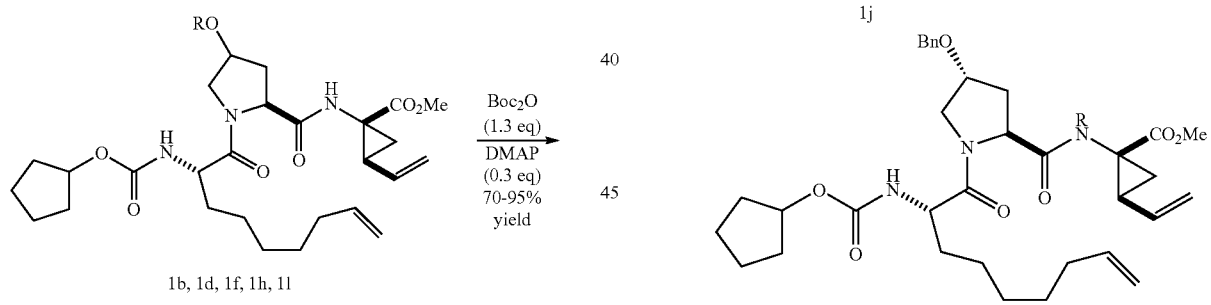

1m (R = Bn): x = 2.2, y = 3.0, 15% yield
1n: (R = H) x = 1.1, y = 2.0, 35% yield Treatment of the non-substituted tripeptide 1b, 1d, 1f, 1h, or 1l with $Boc_2O$ and a catalytic amount of DMAP gave the desired product in good to excellent yield. The di-boc diene 1e' was prepared by treating 1f with excess $Boc_2O$ and DMAP. For diene 1i, since it could not be prepared directly from Boc-protection, acid hydrolysis of compound 1c was used. Di-benzyl substrate 1m was prepared by deprotonation of 1j with 2.2 eq of BuLi followed by reaction with 3.0 eq of BnBr (15% yield after chromatography). Bn-substrate 1n was prepared by treating 1j with 1.1 eq of BuLi followed by 2.0 eq of BnBr (35% yield after chromatography).

Example 9

Deprotection of Macrocycles 2a, 2c and 2e Prepared in Examples 1 to 3

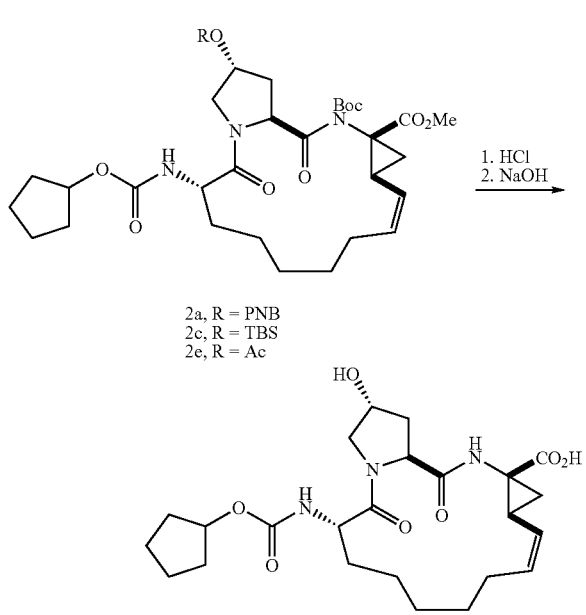

2a, R = PNB
2c, R = TBS
2e, R = Ac

Macrocycles 2a, 2c and 2e were deprotected by treatment with acid followed by base.

Example 10

Preparation Example

Compound 3

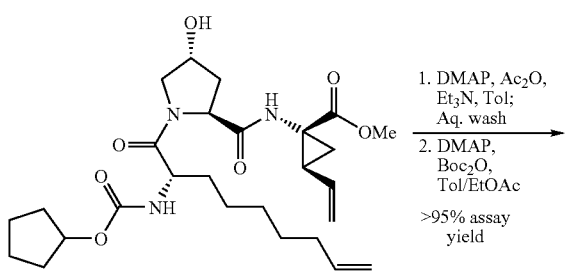

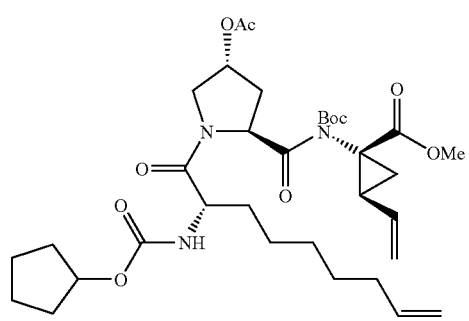

1e

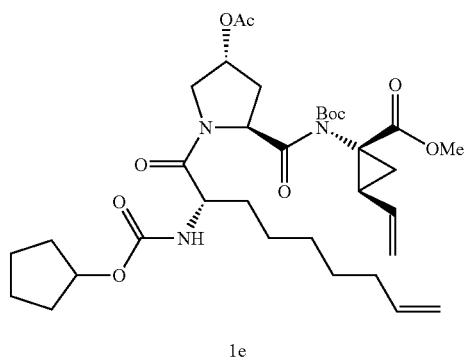

1e

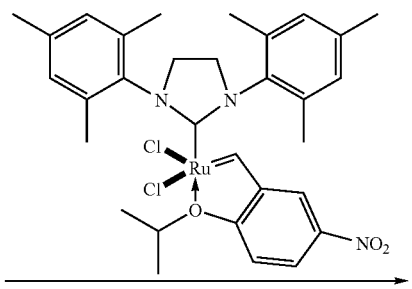

1. The OH-diene substrate (115 g, 1.0 eq), DMAP (2.7 g, 0.1 eq), Et$_3$N (34 g, 1.2 eq) and toluene (450 mL) were added to the reaction vessel. The reaction was cooled to 5° C., and Ac$_2$O (27 g, 1.1 eq) was added over 10 min. After 1 h at 5-10° C., H$_2$O (5 g) was added followed by NaOH solution (16 g in 200 g H$_2$O) at 0° C. over 20 min. The aqueous phase was removed and the organic phase was washed with NaHCO$_3$ solution (10 g in 200 g H$_2$O). The aqueous phase was removed, and the organic phase was distilled to ~300 mL over 30 min. DMAP (8.1 g, 0.3 eq) was added followed by EtOAc (200 mL). At 10° C., Boc$_2$O (65 g, 1.3 eq) in EtOAc (100 mL) was added over 30 min. The reaction was warmed to room temperature over 1.5 h. It was then cooled to 0° C. and HCl solution (20 mL 37% HCl in 230 mL H$_2$O) was added over 5 min. The aqueous phase was removed and the organic phase was washed with H$_2$O (2×200 mL). The organic phase was distilled and the remaining solution (~230 g) was heated to 90° C. Toluene (100 mL) and heptane (1 L) were added and the resulting solution was cooled to room temperature over 1 h, seeded at 40° C. and stirred at room temperature for 1 h. The resulting solid was filtered and washed with heptane (200 mL). Yield 134 g (90%).

-continued

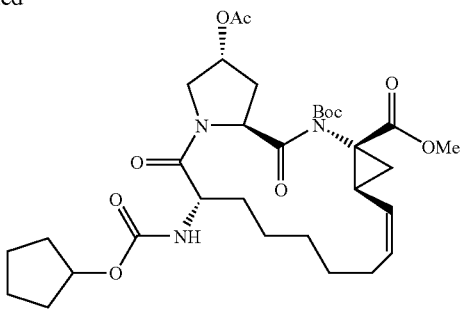

2e

2. Compound 1e from the last step (45 g, 1.0 eq) and toluene (800 mL) were combined in a reaction vessel and degassed for 30 min. The reaction was heated to 110° C. and the Ru catalyst (55 mg in 11 mL anhydrous toluene, 0.1%) was added over 15 min. After 15 min, HPLC indicated complete reaction (>99% conversion, 93% assay yield). Imidazole (1.1 g) was added and the reaction was stirred at 80° C. for 2 h and extracted with HCl (1 M in H₂O, 100 mL) and H₂O (2×100 mL). The organic phase was distilled to ~200 mL and circulated through a funnel (5 inch i.d.) of charcoal (18 g) and diatomaceous earth (5 g) three times.

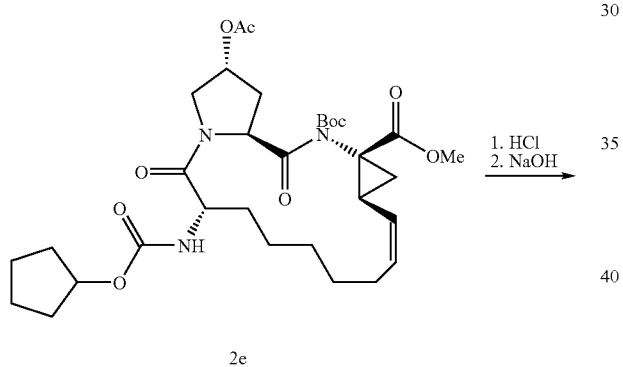

2e

1. HCl
2. NaOH

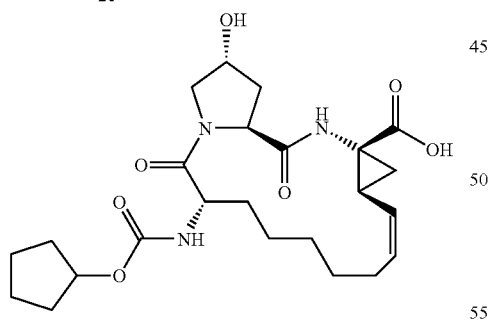

3

3. The toluene solution (~200 mL) of 2e from the above step was distilled to ~50 mL. Methanol (100 mL) was added and the resulting solution distilled. The solvent exchange was repeated three times. Methanol (200 mL) and HCl (12 M, 40 mL) were added and the resulting solution was stirred at 60° C. for 6 h and then cooled to 0° C. NaOH (50 g in 100 mL H₂O) was added slowly over 30 min, and the reaction was stirred at 30° C. for 2 h. The solution was cooled to 0° C., and HCl (12 M, 80 mL) was added over 30 min. EtOAc (200 mL)

was added, and the aqueous layer was removed. The organic phase was washed with H₂O (2×100 mL) and concentrated to ~80 mL. CHCl₃ (15 mL) was added under stirring. After 2 min, a precipitate (solvate of 3 with CHCl₃) was filtered, (32.5 g, corresponding to 26 g of 3, 80% overall of RCM+hydrolysis).

I claim:
1. A compound of the following formula V:

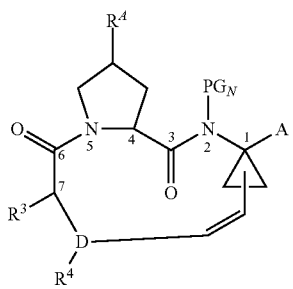

(V)

wherein $R^4$ is OH, O-PG, where PG is a protecting group, or —$OSO_2$—$R^{27}$, wherein $R^{27}$ is selected from phenyl, p-tolyl, p-bromophenyl, p-nitrophenyl, methyl, trifluoromethyl, perfluorobutyl and 2,2,2-trifluoroethyl;

or a group of formula II

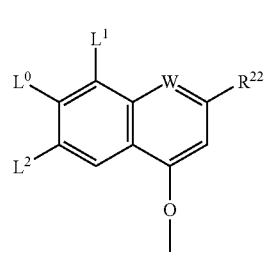

(II)

W is CH or N,
$L^0$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$,
wherein each $R^{23}$ is independently H, $C_{1-6}$ alkyl or $C_{3-6}$ cycloalkyl;
$L^1$, $L^2$ are each independently H, halogen, $C_{1-4}$alkyl, —O—$C_{1-4}$alkyl, or —S—$C_{1-4}$alkyl (the sulfur being in any oxidized state); or
$L^0$ and $L^1$ or $L^0$ and $L^2$ may be covalently bonded to form together with the two C-atoms to which they are linked a 4-, 5- or 6-membered carbocyclic ring wherein one or two (in the case of a 5- or 6-membered ring) —CH$_2$— groups not being directly bonded to each other, may be replaced each independently by —O— or NR$^a$ wherein R$^a$ is H or $C_{1-4}$alkyl, and wherein said ring is optionally mono- or di-substituted with $C_{1-4}$ alkyl;

$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_6$ or $C_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, NO$_2$, N(R$^{25}$)$_2$, NH—C(O)—R$^{25}$; or NH—C(O)—NH—R$^{25}$, wherein each R$^{25}$ is independently: H, $C_{1-6}$ alkyl or $C_{3-6}$ cycloalkyl;

or $R^{24}$ is NH—C(O)—OR$^{26}$ wherein R$^{26}$ is $C_{1-6}$ alkyl or $C_{3-6}$ cycloalkyl;

$R^3$ is hydroxy, NH$_2$, or a group of formula —N(R*)—R$^9$, wherein R* is H or a protecting group, wherein R$^9$ is $C_6$ or 10 aryl, heteroaryl, —C(O)—R$^{20}$, —C(O)—NHR$^{20}$ or —C(O)—OR$^{20}$, wherein R$^{20}$ is $C_{1-6}$ alkyl or $C_{3-6}$ cycloalkyl;

D is a 3 to 7 atom saturated alkylene chain optionally containing one to three heteroatoms independently selected from: O, S or N—R$^{27}$, wherein R$^{27}$ is H, $C_{1-6}$alkyl, $C_{3-6}$cycloalkyl or C(O)R$^{28}$, wherein R$^{28}$ is $C_{1-6}$alkyl, $C_{3-6}$cycloalkyl or $C_6$ or 10 aryl;

$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and A is an amide of formula —C(O)—NH—R$^{11}$, wherein R$^{11}$ is selected from the group consisting of: $C_{1-8}$ alkyl, $C_{3-6}$ cycloalkyl, $C_6$ or 10 aryl, $C_{7-16}$ aralkyl, or SO$_2$R$^{5A}$ wherein R$^{5A}$ is $C_{1-8}$ alkyl, $C_{3-7}$ cycloalkyl, $C_{1-6}$ alkyl-$C_{3-7}$ cycloalkyl;

or A is a carboxylic acid or a pharmaceutically acceptable salt or ester thereof;

and PG$_N$ is a nitrogen protecting group.

2. A compound according to claim 1, wherein:

$R^A$ is selected from: OH, O-PG, where PG is a protecting group, or —OSO$_2$—R$^{27}$, wherein R$^{27}$ is selected from p-tolyl, p-bromophenyl, p-nitrophenyl, methyl, trifluoromethyl, perfluorobutyl and 2,2,2-trifluoroethyl;

or $R^A$ is a group of formula II:

(II)

wherein:
W is N;
$L^0$ is H, $C_{1-6}$ alkyl, $C_{1-6}$ alkoxy, hydroxy, chloro;
$L^1$ and $L^2$ are each independently H, halogen or $C_{1-4}$alkyl;
$R^{22}$ is H, $C_{1-6}$ thioalkyl, $C_{1-6}$ alkoxy, phenyl or Het selected from the group consisting of:

wherein $R^{24}$ is H, $C_{1-6}$ alkyl, NH—R$^{25}$, NH—C(O)—R$^{25}$; NH—C(O)—NH—R$^{25}$, wherein each R$^{25}$ is independently: H, $C_{1-6}$ alkyl, or $C_{3-6}$ cycloalkyl; or NH—C(O)—OR$^{26}$, wherein R$^{26}$ is $C_{1-6}$ alkyl; or $R^3$ is N(R*)—C(O)—OR$^{20}$, wherein R* is H or a protecting group and R$^{20}$ is $C_{1-6}$ alkyl, or $C_{3-6}$ cycloalkyl;

D is a 4 to 6 atom saturated alkylene chain optionally containing one or two heteroatoms independently selected from: O, S or N—R$^{27}$, wherein R$^{27}$ is H, $C_{1-6}$alkyl or $C_{2-7}$acyl;

$R^4$ is H or $C_{1-6}$ alkyl;

A is a carboxylic acid or a pharmaceutically acceptable salt or ester thereof; and and PG$_N$ is a nitrogen protecting group.

3. A compound according to claim 1, wherein:

$R^A$ is selected from: OH, O-PG, where PG is a protecting group, or —OSO$_2$—R$^{27}$, wherein R$^{27}$ is selected from p-tolyl, p-bromophenyl, p-nitrophenyl, methyl, trifluoromethyl, perfluorobutyl and 2,2,2-trifluoroethyl;

$R^3$ is N(R*)—C(O)—OR$^{20}$, wherein R* is H or a protecting group and R$^{20}$ is butyl, cyclobutyl or cyclopentyl;

$R^4$ is H or $C_{1-6}$alkyl;

D is a 5 atom saturated alkylene chain;

A is a carboxylic acid or a pharmaceutically acceptable salt or ester thereof; and and PG$_N$ is —COOC$_{1-6}$alkyl.

4. A compound according to claim 1, wherein:

$R^A$ is selected from: OH, p-nitrobenzoyloxy, t-butyldimethylsilyloxy, acetyloxy, benzyloxy and —OSO$_2$—R$^{27}$, wherein R$^{27}$ is p-bromophenyl;

$R^3$ is NH—C(O)—OR$^{20}$, wherein R$^{20}$ is cyclopentyl;

$R^4$ is H or $C_{1-3}$ alkyl;

D is a 5 atom saturated alkylene chain;

A is a carboxylic acid or a pharmaceutically acceptable salt or ester thereof; and and PG$_N$ is tert-butyloxycarbonyl.

5. A process for preparing a compound of formula V as set forth in claim 1, said process comprising cyclizing a compound of formula IV in the presence of a suitable catalyst in a suitable organic solvent to obtain macrocyclic compound V, wherein $R^A$, $R^3$, $R^4$, D, A, and $PG_N$ are as defined in claim 1 and each $R^5$ in formula IV is independently selected from H, $C_{1-6}$alkyl and $C_{3-6}$cycloalkyl:

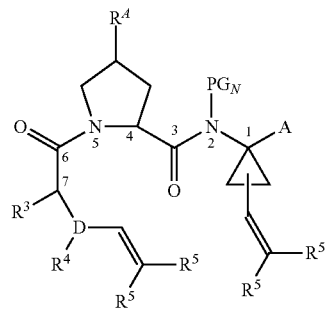

(IV)

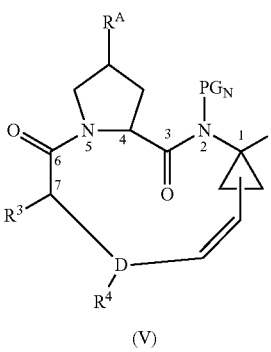

(V)

6. A process according to claim 5, wherein the catalyst is selected from the compounds of formula A, B, C, D or E:

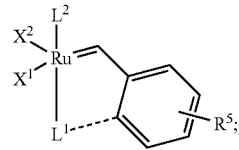

(A)

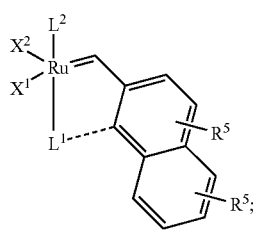

(B)

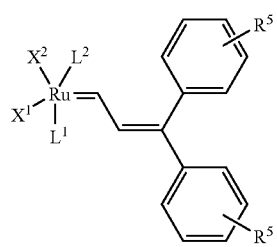

(C)

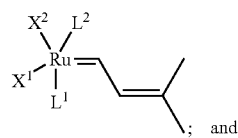

(D)

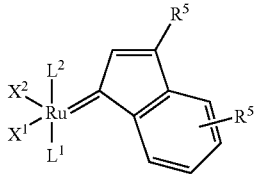

(E)

wherein $X^1$ and $X^2$ each independently represent an anionic ligand, $L^1$ represents a neutral electron donor ligand which is bonded to the ruthenium atom and is optionally bonded to the phenyl group, and $L^2$ represents a neutral electron donor ligand which is bonded to the ruthenium atom;

and $R^5$ is selected from one or more substituents on the benzene ring, each substituent independently selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$cycloalkyl, $C_{1-6}$alkoxy, hydroxyl, halogen, nitro, imino, oxo, thio or aryl; and wherein $X^2$ and $L^2$ may optionally together form a chelating bidentate ligand.

7. A process according to claim 5, wherein the catalyst is selected from the compounds of formula A-1 and A-2:

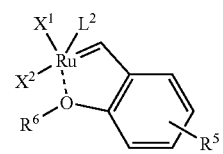

(A-1)

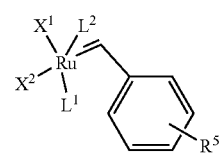

(A-2)

wherein:

$L^1$ is a trisubstituted phosphine group of the formula $PR_3$, wherein R is selected from $C_{1-6}$alkyl and $C_{3-8}$cycloalkyl, $L^2$ is a trisubstituted phosphine group of the formula $PR_3$, wherein R is selected from $C_{1-6}$alkyl and $C_{3-8}$cycloalkyl, or $L^2$ is a group of the formula A or B:

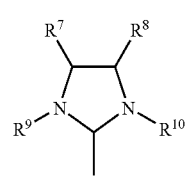

(A)

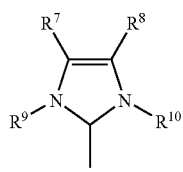

(B)

wherein

R⁷ and R⁸ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group; and R⁹ and R¹⁰ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group, each optionally substituted by one, two or three groups selected from hydrogen, $C_{1-6}$alkyl, halo$C_{1-6}$ alkyl, HS—$C_{1-6}$alkyl, HO—$C_{1-6}$alkyl, perfluoro$C_{1-6}$ alkyl, $C_{3-6}$ cycloalkyl, $C_{1-6}$alkoxy, hydroxyl, halogen, nitro, imino, oxo, thio or aryl;

X¹ and X² each independently represent a halogen atom;

R⁵ represent hydrogen or nitro; and

R⁶ represents a $C_{1-6}$ alkyl group.

8. A process according to claim 5, wherein the catalyst is selected from the following compounds:

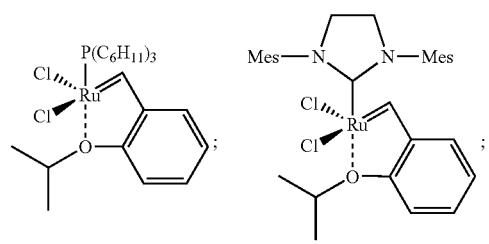

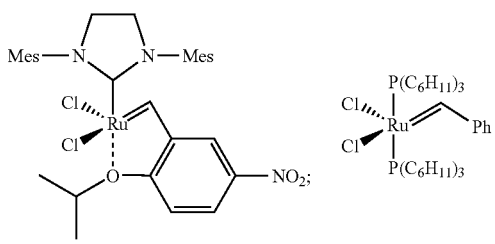

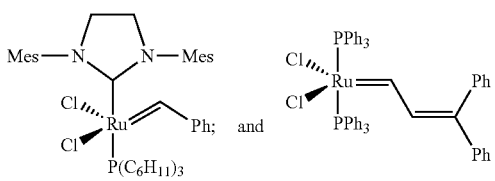 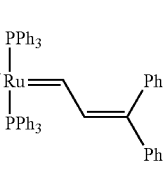

where Ph is phenyl and Mes is 2,4,6-trimethylphenyl.

9. A process of using a compound of formula V as set forth in claim 1 to prepare a compound of the following formula I, said process comprising subjecting compound V to deprotection conditions to obtain a compound of formula I:

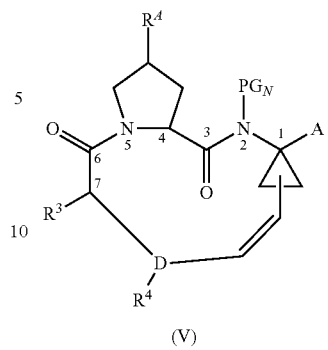

(V)

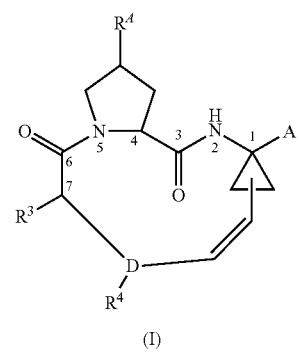

(I)

wherein $R^A$, R³, R⁴, D, A, and $PG_N$ are as defined in claim 1.

10. A compound of the following formula (IV):

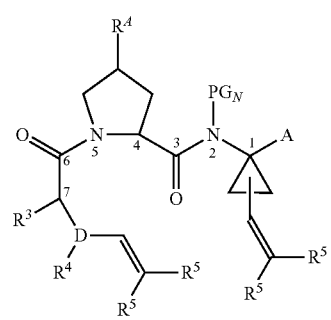

(IV)

wherein $R^A$ is OH, O-PG, where PG is a protecting group, or —OSO₂—R²⁷, wherein R²⁷ is selected from phenyl, p-tolyl, p-bromophenyl, p-nitrophenyl, methyl, trifluoromethyl, perfluorobutyl and 2,2,2-trifluoroethyl;

or a group of formula II

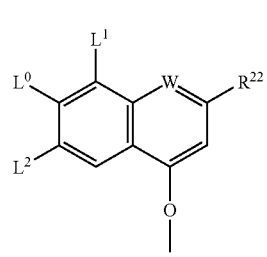

(II)

W is CH or N,

L⁰ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$L^1$, $L^2$ are each independently H, halogen, $C_{1-4}$alkyl, —O—$C_{1-4}$alkyl, or —S—$C_{1-4}$alkyl (the sulfur being in any oxidized state); or $L^0$ and $L^1$ or $L^0$ and $L^2$ may be covalently bonded to form together with the two C-atoms to which they are linked a 4-, 5- or 6-membered carbocyclic ring wherein one or two (in the case of a 5- or 6-membered ring)-CH$_2$— groups not being directly bonded to each other, may be replaced each independently by —O— or NR$^a$ wherein R$^a$ is H or $C_{1-4}$alkyl, and wherein said ring is optionally mono- or di-substituted with $C_{1-4}$ alkyl;

$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_6$ or $C_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, NO$_2$, N(R$^{25}$)$_2$, NH—C(O)—R$^{2}$; or NH—C(O)—NH—R$^{25}$, wherein each $R^{25}$ is independently: H, $C_{1-6}$ alkyl or $C_{3-6}$ cycloalkyl;

or $R^{24}$ is NH—C(O)—OR$^{26}$ wherein $R^{26}$ is $C_{1-6}$ alkyl or $C_{3-6}$ cycloalkyl;

$R^3$ is hydroxy, NH$_2$, or a group of formula —N(R*)—R$^9$, wherein R* is H or a protecting group and R$^9$ is $C_6$ or 10 aryl, heteroaryl, —C(O)—R$^{20}$, —C(O)—NHR$^{20}$ or —C(O)—OR$^{20}$, wherein $R^{20}$ is $C_{1-6}$ alkyl or $C_{3-6}$ cycloalkyl;

D is a 3 to 7 atom saturated alkylene chain optionally containing one to three heteroatoms independently selected from: O, S or N—R$^{27}$, wherein $R^{27}$ is H, $C_{1-6}$alkyl, $C_{3-6}$cycloalkyl or C(O)R$^{28}$, wherein $R^{28}$ is $C_{1-6}$alkyl, $C_{3-6}$cycloalkyl or $C_{6 \text{ or } 10}$ aryl;

$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl;

each $R^5$ is independently selected from H, $C_{1-6}$alkyl and $C_{3-6}$cycloalkyl;

A is an amide of formula —C(O)—NH—R$^{11}$, wherein $R^{11}$ is selected from the group consisting of: $C_{1-8}$ alkyl, $C_{3-6}$ cycloalkyl, $C_6$ or 10 aryl, $C_{7-16}$ aralkyl, or SO$_2$R$^{5A}$ wherein $R^{5A}$ is $C_{1-8}$ alkyl, $C_{3-7}$ cycloalkyl, $C_{1-6}$ alkyl-$C_{3-7}$ cycloalkyl;

or A is a carboxylic acid or a pharmaceutically acceptable salt or ester thereof;

and PG$_N$ is a nitrogen protecting group.

11. A compound according to claim 10, wherein:

$R^A$ is selected from: OH, O-PG, where PG is a protecting group, or —OSO$_2$—R$^{27}$, wherein $R^{27}$ is selected from p-tolyl, p-bromophenyl, p-nitrophenyl, methyl, trifluoromethyl, perfluorobutyl and 2,2,2-trifluoroethyl;

or $R^A$ is a group of formula II:

(II)

wherein:

W is N;

$L^0$ is H, $C_{1-6}$ alkyl, $C_{1-6}$ alkoxy, hydroxy, chloro;

$L^1$ and $L^2$ are each independently H, halogen or $C_{1-4}$alkyl;

$R^{22}$ is H, $C_{1-6}$ thioalkyl, $C_{1-6}$ alkoxy, phenyl or Het selected from the group consisting of:

wherein $R^{24}$ is H, $C_{1-6}$ alkyl, NH—R$^{25}$, NH—C(O)—R$^{25}$; NH—C(O)—NH—R$^{25}$, wherein each $R^{25}$ is independently: H, $C_{1-6}$ alkyl, or $C_{3-6}$ cycloalkyl;

or NH—C(O)—OR$^{26}$, wherein $R^{26}$ is $C_{1-6}$ alkyl; or $R^3$ is N(R*)—C(O)—OR$^{20}$, wherein R* is H or a protecting group and $R^{20}$ is $C_{1-6}$ alkyl, or $C_{3-6}$ cycloalkyl;

D is a 4 to 6 atom saturated alkylene chain optionally containing one or two heteroatoms independently selected from: O, S or N—R$^{27}$, wherein $R^{27}$ is H, $C_{1-6}$alkyl or $C_{2-7}$acyl;

$R^4$ is H or $C_{1-6}$ alkyl;

each $R^5$ is independently selected from H, $C_{1-6}$alkyl and $C_{3-6}$cycloalkyl;

A is a carboxylic acid or a pharmaceutically acceptable salt or ester thereof; and and PG$_N$ is a nitrogen protecting group.

12. A compound according to claim 10, wherein:

$R^A$ is selected from: OH, O-PG, where PG is a protecting group, or —OSO$_2$—R$^{27}$, wherein $R^{27}$ is selected from p-tolyl, p-bromophenyl, p-nitrophenyl, methyl, trifluoromethyl, perfluorobutyl and 2,2,2-trifluoroethyl;

$R^3$ is N(R*)—C(O)—OR$^{20}$, wherein R* is H or a protecting group and $R^{20}$ is butyl, cyclobutyl or cyclopentyl;

$R^4$ is H or $C_{1-6}$ alkyl;

each $R^5$ is independently selected from H;

D is a 5 atom saturated alkylene chain;

A is a carboxylic acid or a pharmaceutically acceptable salt or ester thereof; and and PG$_N$ is —COOC$_{1-6}$alkyl.

13. A compound according to claim 10, wherein:

$R^A$ is selected from: OH, p-nitrobenzoyloxy, t-butyldimethylsilyloxy, acetyloxy, benzyloxy and —OSO$_2$—R$^{27}$, wherein $R^{27}$ is p-bromophenyl;

$R^3$ is NH—C(O)—OR$^{20}$, wherein $R^{20}$ is cyclopentyl;

$R^4$ is H or $C_{1-3}$ alkyl;

each $R^5$ is independently selected from H;

D is a 5 atom saturated alkylene chain;

A is a carboxylic acid or a pharmaceutically acceptable salt or ester thereof; and and PG$_N$ is tert-butyloxycarbonyl.

14. A process for preparing a compound of formula IV according to claim 10, said process comprising subjecting compound III to nitrogen-protection conditions to obtain a compound of formula IV:
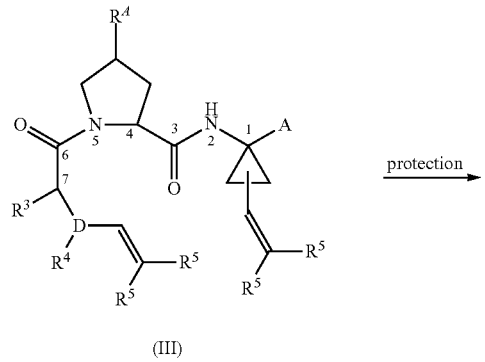
(III)
protection →
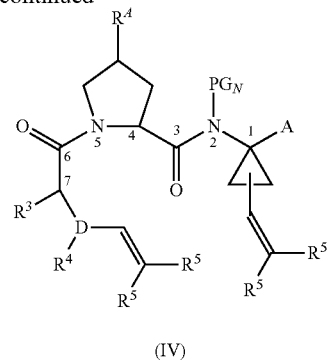
(IV)
wherein $R^A$, $R^3$, $R^4$, $R^5$, D, A, and $PG_N$ are as defined in claim 10.
* * * * *